United States Patent
Vicente et al.

(10) Patent No.: US 11,713,289 B2
(45) Date of Patent: Aug. 1, 2023

(54) COMPOSITION OF CATALYSTS FOR CONVERSION OF ETHANOL TO N-BUTANOL AND HIGHER ALCOHOLS

(71) Applicant: VIRIDIS CHEMICAL, LLC, Kingwood, TX (US)

(72) Inventors: Brian C. Vicente, Santa Barbara, CA (US); Peter K. Stoimenov, Goleta, CA (US); Sagar B. Gadewar, Sugar Land, TX (US)

(73) Assignee: VIRIDIS CHEMICAL, LLC, Kingwood, TX (US)

( * ) Notice: Subject to any disclaimer, the term of this patent is extended or adjusted under 35 U.S.C. 154(b) by 69 days.

(21) Appl. No.: 17/048,071

(22) PCT Filed: Apr. 16, 2019

(86) PCT No.: PCT/US2019/027607
§ 371 (c)(1),
(2) Date: Oct. 15, 2020

(87) PCT Pub. No.: WO2019/204259
PCT Pub. Date: Oct. 24, 2019

(65) Prior Publication Data
US 2021/0147327 A1  May 20, 2021

Related U.S. Application Data

(60) Provisional application No. 62/658,141, filed on Apr. 16, 2018.

(51) Int. Cl.
| | | |
|---|---|---|
| *C07C 29/158* | (2006.01) | |
| *B01J 23/44* | (2006.01) | |
| *B01J 23/72* | (2006.01) | |
| *B01J 35/00* | (2006.01) | |
| *B01J 35/10* | (2006.01) | |
| *B01J 37/08* | (2006.01) | |

(52) U.S. Cl.
CPC ............ *C07C 29/158* (2013.01); *B01J 23/44* (2013.01); *B01J 23/72* (2013.01); *B01J 35/0006* (2013.01); *B01J 35/1009* (2013.01); *B01J 35/1014* (2013.01); *B01J 35/1038* (2013.01); *B01J 37/08* (2013.01)

(58) Field of Classification Search
None
See application file for complete search history.

(56) References Cited

U.S. PATENT DOCUMENTS

| | | | |
|---|---|---|---|
| 7,417,005 B2 | 8/2008 | Vierheilig | |
| 7,705,192 B2* | 4/2010 | Kourtakis | ............... C07C 29/34 568/902.2 |
| 7,745,672 B2* | 6/2010 | Kourtakis | ............... C07C 29/34 568/902.2 |
| 8,071,823 B2 | 12/2011 | Ozer et al. | |
| 10,669,221 B2* | 6/2020 | Vicente | ............... B01J 37/08 |
| 2010/0160693 A1* | 6/2010 | Kourtakis | ............... C07C 29/34 568/905 |
| 2010/0286455 A1* | 11/2010 | Ozer | ............... C07C 29/34 568/902 |
| 2010/0298614 A1* | 11/2010 | Ozer | ............... C07C 29/34 568/905 |
| 2015/0273449 A1* | 10/2015 | Stoimenov | ............... B01J 29/48 423/714 |
| 2016/0136623 A1* | 5/2016 | Radlowski | ............... B01J 31/34 502/211 |
| 2017/0320799 A1 | 11/2017 | Corma Canos et al. | |

FOREIGN PATENT DOCUMENTS

| | | | | |
|---|---|---|---|---|
| WO | WO-2009097310 A1 * | 8/2009 | ............ | C07C 29/34 |
| WO | 2017031439 A1 | 2/2017 | | |
| WO | WO-2017031439 A1 * | 2/2017 | ............ | B01J 21/10 |
| WO | 2019204259 A1 | 10/2019 | | |

OTHER PUBLICATIONS

Y. Xi et al., 268 Journal of Catalysis, 307-317 (2009) (Year: 2009).*
L. Vieille et al., 15 Chemistry of Materials, 4361-4368 (2003) (Year: 2003).*
X. Qiu et al., 287 Journal of Hazardous Materials, 268-277 (2015) (Year: 2015).*
International Preliminary Report on Patentability dated Oct. 29, 2020, for International Application No. PCT/US2019/027607, filed on Apr. 16, 2019.
International Search Report and Written Opinion dated Aug. 2, 2019, for International Application No. PCT/US2019/027607, filed on Apr. 16, 2019.

* cited by examiner

*Primary Examiner* — Alexander R Pagano
(74) *Attorney, Agent, or Firm* — Conley Rose, P.C.; Andrew M. Metrailer

(57) ABSTRACT

A method of producing a catalyst comprises forming a decomposed material comprising a decomposed hydrotalcite, a decomposed hydrocalumite, or a combination of both, combining the decomposed material with a mixture to form a catalyst mixture, and heating the catalyst mixture to convert the metal salt to a metal oxide. The mixture comprises a metal salt and a chelating agent, and the resulting metal oxide combined with the decomposed material forms the catalyst.

22 Claims, 12 Drawing Sheets

COMPOSITION OF CATALYSTS FOR CONVERSION OF ETHANOL TO N-BUTANOL AND HIGHER ALCOHOLS

CROSS-REFERENCE TO RELATED APPLICATIONS

The present application is a filing under 35 U.S.C. 371 as the National Stage of International Application No. PCT/US2019/027607, filed on Apr. 16, 2019 and entitled, "COMPOSITION OF CATALYSTS FOR CONVERSION OF ETHANOL TO N-BUTANOL AND HIGHER ALCOHOLS," which claims the benefit of and claims priority to U.S. Provisional Application No. 62/658,141 filed Apr. 16, 2018 and entitled "Composition of Catalysts for Conversion of Ethanol to N-Butanol and Higher Alcohols," both of which are incorporated herein in their entirety for all purposes.

BACKGROUND

N-Butanol and ethyl acetate are commercially significant organic compounds having use in a wide variety of applications and which are produced in quantities exceeding 1 million tons per year. N-Butanol can be produced from several different reactions. The most common method for making n-butanol is hydroformylation. Propylene reacts with syngas over cobalt or rhodium catalysts at high pressures to produce an aldehyde (butyraldehyde), which is then hydrogenated over a nickel catalyst to give the alcohol. The drawbacks of such a process include the high energy costs associated with the generation of syngas, the use of a potentially non-renewable feedstocks (propylene and syngas are typically sourced from petroleum and natural gas, respectively), and the complexity of the process which requires multiple reactors and, typically, homogenous hydroformylation catalysts.

N-Butanol can also be produced from an aldol condensation reaction followed by hydrogenation. This method converts acetaldehyde to butanols, although the high toxicity and limited availability of acetaldehyde make such a process unattractive. Some processes, for example U.S. Pat. Nos. 1,992,480 and 8,071,823 both of which are incorporated herein by reference in their entirety, utilize a gas phase reaction to provide butanol.

Direct fermentation of sugars is another process for production of n-butanol. As a bioprocess this method suffers from long process times and large separation requirements in addition to the need for specialized microbes necessary to make butanol directly from sugars.

SUMMARY OF THE DISCLOSURE

In some embodiments, a method of producing a catalyst comprises: forming a decomposed material comprising a decomposed hydrotalcite, a decomposed hydrocalumite, or a combination of both, combining the decomposed material with a mixture to form a catalyst mixture, and heating the catalyst mixture to convert the metal salt to a metal oxide. The mixture comprises a metal salt and a chelating agent, and the resulting metal oxide combined with the decomposed material forms the catalyst.

In some embodiments, a method of producing a catalyst comprises combining a material with a mixture to form a catalyst mixture, decomposing the catalyst mixture above a decomposition temperature of the material to form a decomposed material, and heating the catalyst mixture to convert the metal salt to a metal oxide. The material comprises hydrotalcite, hydrocalumite, or both, and the mixture comprises a metal salt and a chelating agent. The resulting metal oxide combined with the decomposed material forms the catalyst.

In some embodiments, a method of producing a catalyst comprises decomposing material to form a decomposed hydrotalcite, a decomposed hydrocalumite, or a combination of both, combining the decomposed material with a mixture to form a catalyst mixture, and heating the catalyst mixture to convert the metal salt to a metal oxide. The mixture comprises a metal salt; and the resulting metal oxide combined with the decomposed material forms the catalyst. At least one of the decomposing or the heating comprises applying heat at a temperature between 600° C. and 750° C.

In some embodiments, a method for producing a higher alcohol comprises contacting a reactant comprising ethanol with a catalyst at a reaction temperature and pressure sufficient to produce a reaction product, separating the unreacted ethanol from the reaction product, separating substantially all of the ester from the unreacted ethanol to form an ethanol recycle stream, and recycling the ethanol recycle stream to contact the catalyst. The catalyst comprises a decomposed hydrotalcite, a decomposed hydrocalumite, or a combination of both mixed with one or more metal oxides, and the reaction product comprises a higher alcohol, unreacted ethanol, and an ester.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1:
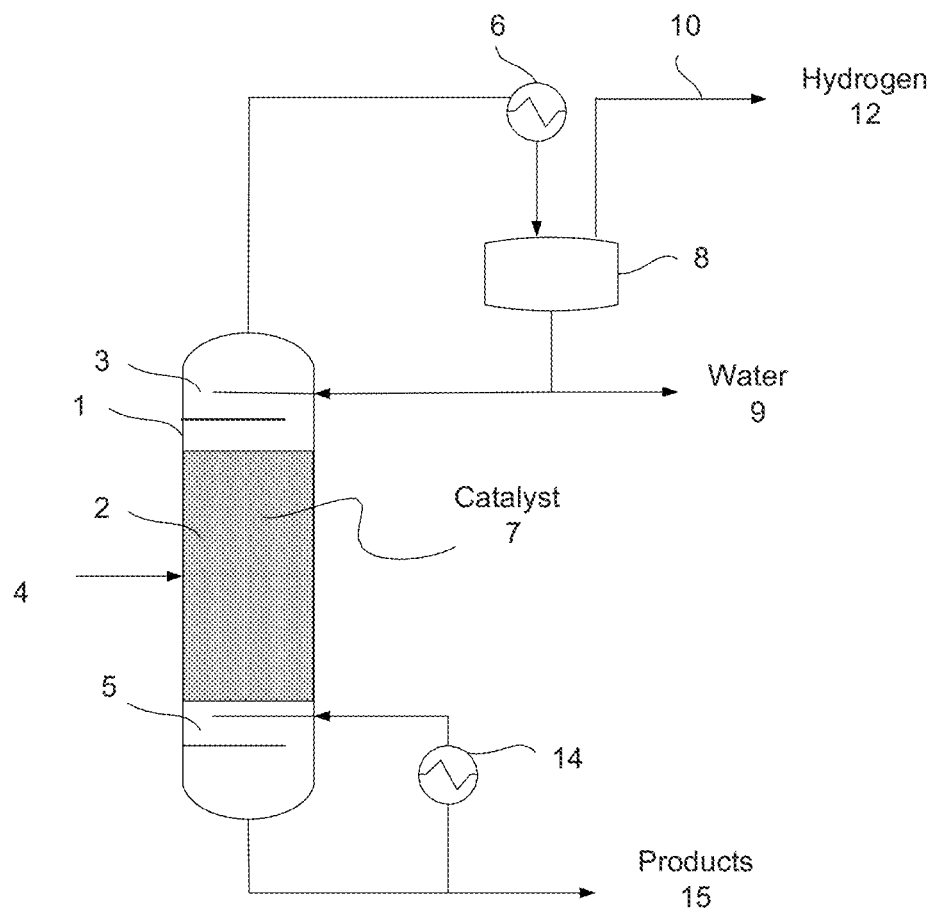
FIG. 1 shows a simplified schematic of a reactive distillation system according to an embodiment.

The present application is directed to a variety of catalysts and methods of producing the catalysts so that the catalysts are capable of catalytically converting inexpensive alcohol feedstock such as bio-renewable ethanol to higher value, larger carbon number, primary alcohols, preferably n-butanol and higher alcohols (e.g., higher homolog members in the $C_6$-$C_{13}$ carbon range of saturated alcohols) along with methods and processes for the creation of the catalysts. These alcohols can have multiple high volume applications as plasticizers, surfactants, co-surfactants and property improving additives. The alcohols can be further converted to other desirable, high value chemical products such as esters, ethers, or olefins which also have a multitude of applications.

As used herein, higher alcohols refer to saturated alcohols having a higher molecular weight than the alcohol forming the reactant in the formation process. In some embodiments, the higher alcohols can include $C_4$-$C_{20}$ alcohols, or even higher alcohols. This process is beneficial as it provides an improved commercial method of upgrading ethanol to higher alcohols such as n-butanol, which are more valuable products. This improved commercial process may be used where there is a supply and/or a surplus supply of ethanol. Further, this process reduces and/or eliminates the need for separate syngas and n-butyraldehyde plants to provide the precursors for the butanol production process, and reduces and/or eliminates reliance on syngas as a precursor, which is expensive to produce and requires a non-renewable resource when obtained from petroleum and natural gas. This process also reduces and/or eliminates the need for a separate acetaldehyde plant to provide the precursors for the butanol production process, and reduces and/or eliminates reliance on highly toxic acetaldehyde.

Although there is some literature on catalytic conversion of ethanol to n-butanol, the process is not practiced commercially as described. There is a similar process described in literature and known for some time where the reaction is performed in a liquid phase in a batch reactor in the presence of catalyst (e.g., using the Guerbet reaction). The process is not practiced commercially due to loss of catalyst due to side reactions and the formation of many undesirable products.

Currently, n-butanol and higher alcohols are made by hydroformylation of olefins such as ethylene, propylene and butylene followed by hydrogenation. Disadvantages to the current technology include the generation of significant quantities of branched alcohols, the use of petroleum derived starting materials, and generally low selectivity.

The catalysts that are described herein are prepared in a way that is different from the preparations described in literature. The difference in their preparation may create a different structure that enables a higher performance in comparison with similarly prepared catalysts.

The mechanism for the conversion of ethanol to n-butanol (and/or higher alcohols) is a multi-step reaction that requires two different catalytic functions. The catalysts for this process must perform both alcohol dehydrogenation/aldehyde hydrogenation and aldol condensation.

Dehydrogenation: $C_2H_5OH \leftrightarrows CH_3CHO + H_2$ (dehydrogenation/hydrogenation catalyst component) (Eq. 1)

Aldol condensation: $CH_3CHO + CH_3CHO \rightarrow CH_3CH(OH)CH_2CHO$ (aldol catalyst component) (Eq. 2)

Dehydration: $CH_3CH(OH)CH_2CHO \rightarrow CH_3CH=CHCHO + H_2O$ (spontaneous, no catalyst) (Eq. 3)

Hydrogenation: $CH_3CH=CHCHO + 2 H_2 \leftrightarrows CH_3CH_2CH_2CHO$ (dehydrogenation/hydrogenation catalyst component) (Eq. 4)

The overall reaction is a dehydration:

$$2\ C_2H_5OH \rightarrow n\text{-}C_4H_9OH + H_2O$$

It is worth noting that due to the relatively complicated mechanism, simple dehydration catalysts, such as alumina and silica do not form any n-butanol when ethanol is passed over them. While not intending to be limited by theory, when higher alcohols are generated, the chain elongation may occur from further aldol condensation of the unsaturated aldehyde (Eq. 3) to form linear primary alcohols:

$CH_3CH=CHCHO + CH_3CHO \rightarrow CH_3CH=CHCH=CHCHO + H_2O$ (Eq. 5)

$CH_3CH=CHCH=CHCHO + 3H_2 \rightarrow CH_3CH_2CH_2CH_2CH_2OH$ (Eq. 6)

or through the reaction of butyraldehyde with acetaldehyde to form the corresponding branched hexanol (2-ethylbutanol):

$CH_3CH_2CH_2CHO + CH_3CHO \rightarrow CH_3CH_2CHCH_2C(CH_3CH=)CHO + H_2O$ (Eq. 7)

$CH_3CH_2CHCH_2C(CH_3CH=)CHO + 2 H_2 \rightarrow CH_3CH_2CHCH_2C(CH_3CH_2)CH_2OH$ (Eq. 8)

In some embodiments, the catalyst described here can have the two components: 1) hydrogenation/dehydrogenation and 2) aldol condensation.

Various elements can act as the hydrogenation/dehydrogenation component. In an embodiment, the catalyst can comprise Pt, Pd, Cu, $Cr_2O_3$, Ni, Fe, Ru, Rh, Co, $Cu_2Cr_2O_5$ either standalone or dispersed on various supports. In some embodiments, the catalyst can comprise Pd and/or Cu either standalone or dispersed on various supports. Supports may be important in hydrogenation catalysis as they may potentiate the activity or selectively reduce the activity of the hydrogenation catalyst.

In an embodiment, a thermally decomposed hydrocarbonate and/or hydrotalcite or a thermally decomposed hydrotalcite pretreated with metal salts to increase the basicity can be used for the aldol condensation coupling catalyst component. Hydrotalcite has a general formula:

$$(M^{2+}_{1-x}M^{3+}_x(OH)_2)(A^{n-}_{x/n}) \cdot yH_2O$$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Hydrotalcite is a mineral that has a peculiar lamellar structure where a magnesium-aluminum mixed oxide forms a backbone of a structure with layers of exchangeable counter anions between the metal oxide sheets. The hydrotalcite used for preparation of the catalyst can be obtained commercially as a synthetic hydrotalcite, although naturally occurring hydrotalcite can have substantially the same catalytic activity. The commercial hydrotalcite generally has a mixture of carbonate and hydroxide anions as counter ions, although these anions can be changed to improve or optimize reactivity.

An alternative to hydrotalcite is hydrocalumite, which has a different range of composition yet has a similar double hydroxide layer structure (e.g. $Ca_2Al(OH)_6[Cl_{1-x}(OH)_x]\cdot 3(H_2O)$). Hydrocalumite used for catalyst preparation would be used in the same fashion as the hydrotalcite except higher temperatures will be used for its decomposition (400° C.-1000° C.). While portions of the present application describe catalysts prepared with hydrotalcite, both natural or synthetic hydrocalumite can be used in the catalysts described herein in place of hydrotalcite or in combination with hydrotalcite.

The catalyst of the present description can be prepared using several processes as described below.

1. Preparation of Aldol Condensation Component.

Upon heating, the hydrotalcite decomposes irreversibly above about 350° C. This decomposition is accompanied by loss of crystallinity and the organized lamellar layer structure collapses, generating a very intimate magnesium aluminum oxide mixture. Subsequently, the mixture may crystallize in new phases such as meixnerite ($Mg_6Al_2(OH)_{18}\cdot 4H_2O$). The resulting magnesium aluminum oxide mixture is referred to as a decomposed hydrotalcite, which can be treated in various ways in subsequent processes, including the addition of the hydrogenation/dehydrogenation component. The degree of decomposition, crystallinity loss and structural changes varies with temperature and duration of the heat treatment. In some embodiments, the range of decomposition temperatures can be between about 350° C. and about 800° C., between about 450° C. and about 500° C., or alternatively at a temperature of about 475° C. In some embodiments, the decomposition can be carried using a calcination process as described in more detail herein.

2. Preparation of Aldol Condensation Component.

Hydrotalcite can be mixed with a metal salt such as alkaline earth or alkaline metal nitrate, chloride, acetate, formate or any other soluble salt of the desired metal. Most preferable are organic acid salts as they decompose quickly and completely to form the corresponding metal oxides which may react further with the thermally decomposed hydrotalcite product. The salts can be delivered as relatively concentrated solutions added to an aqueous or ethanol/water suspension of the thermally decomposed hydrotalcite or hydrotalcite (e.g., as a slurry) to facilitate the wetting of the hydrotalcite particles. The slurry can be heated to about 105° C. until dry followed by annealing at elevated temperature (e.g., between about 300° C. and about 500° C.). The heating generates a thermally decomposed hydrotalcite containing a higher amount (in relation to stoichiometric content in the hydrotalcite) of strongly basic metal oxide such as magnesium or calcium oxide. In some embodiments, the decomposition can be carried using a calcination process as described in more detail herein.

In an embodiment, the decomposed hydrotalcite with or without the metal salt treatment can comprise a variety of structures including a meixnerite ($Mg_6Al_2(OH)_{18}\cdot 4H_2O$) phase.

The decomposed hydrotalcite with or without the metal salt treatment is treated further with an aqueous solution comprising a desired hydrogenation/dehydrogenation component. For example, the decomposed hydrotalcite with or without the metal salt treatment can be further treated with Pd, Cu, or another of the desired hydrogenation/dehydrogenation metal salts as precursors listed herein. In some embodiments, the metal salt can be used with a complexing or chelating agent to improve dispersion, as described in more detail herein. In an embodiment, the decomposed hydrotalcite can be treated by incipient wetting method or by drying of a slurry of the decomposed hydrotalcite material in the corresponding metal salt solution. After drying at a temperature between about 85° C. and about 105° C., the material can either be heated to high temperature (to decompose the metal salt to corresponding metal (e.g. Pd, Pt) or metal oxides ($Fe_2O_3$ and CuO)). The heating can be done in air, in an inert atmosphere (e.g. nitrogen) or in a reducing atmosphere (e.g. in the presence of hydrogen). The same conversion of metal salt to metal or metal oxide can be achieved by chemical means without heating in air such as by reduction with gaseous hydrogen, reduction with an aqueous or organic solution of reactants such as hydrazine, hydroxylamine, formaldehyde, ascorbic acid (vitamin C), sodium dithionite, sodium borohydride or other common reducing agents.

In an embodiment of the preparation of the catalyst material as described above, the process can begin with commercially available hydrotalcite. The hydrotalcite can be decomposed prior to loading the dehydrogenation/hydrogenation component. The dehydrogenation/hydrogenation component can then be loaded on an already decomposed hydrotalcite, and thus, the hydrogenation catalyst component can be generated on the surface of the thermally decomposed hydrotalcite. The ratio of hydrogenation catalyst component to hydrotalcite can be varied at will and there are no limitations as in the end the two catalyst components generate a physical mixture of metal particles (e.g. Pd) loaded on the surface of the mixture of intimate magnesium and aluminum oxides generated from the decomposition of the hydrotalcite. In some embodiments, the catalyst material can comprise Pd having a loading between about 0.01 wt % and about 5 wt % of the catalyst material.

The catalyst prepared according to the present disclosure is distinct from a catalyst that is prepared by first loading the dehydrogenation/hydrogenation metal component into the hydrotalcite mineral structure (e.g., the Pd(II) or Cu(II)). A catalyst having the metal component first loaded into the hydrotalcite can be created by loading the metal component (e.g. Pd(II) introduced as $Pd(NO_3)_2$) into the crystal structure of the hydrotalcite. The metal ions (e.g., Pd(II) ions) can then exchange with the $M^{2+}$ component isomorphically in the Mg(II) sites in the hydrotalcite structure. The catalyst that catalyzes the conversion of ethanol to n-butanol with the M(II) replacing the Mg(II)) is then generated upon thermal decomposition of the exchanged structure. The use of a process that first loads the dehydrogenation/hydrogenation component into the mineral catalyst limits the amount of the components that may be introduced before the hydrotalcite structure becomes difficult, if not impossible, to form.

Thus the preparation process described herein differs in that the hydrogenation component is added after the hydrotalcite structure has already collapsed (e.g., due to thermal decomposition, etc.), which is expected to provide a different dispersion of the two components within the catalyst and thereby improve the performance of the catalyst. While not intending to be limited by theory, it is expected that decomposing the hydrotalcite first may generate a coarser dispersion of the components. While this can result in a decreased performance in some instances, it has been unexpectedly found to improve the conversion to n-butanol in the current applications. Further, the inclusion of the dehydrogenation/hydrogenation component after the hydrotalcite is decomposed may provide for a broader range of loadings that can exceed the stoichiometric limit present in an ion exchanged hydrotalcite. As noted above, the catalyst material can also use hydrocalumite alone or in combination with the hydrotalcite in any of the preparation methods described herein.

In an embodiment, the hydrotalcite can be treated with an alkaline-earth or alkaline salt prior to being decomposed. In this embodiment, the hydrotalcite can be combined and suspended in a slurry of metal salt solution such as Mg-acetate or Ca-acetate and/or other alkaline or alkaline earth salts. The slurry is homogenized by mixing and heated to dryness followed by decomposition at high temperature, which causes hydrotalcite to thermally decompose (e.g., lose crystallinity and have the crystal structure collapse) as well as the metal salts to form corresponding oxides (e.g. MgO, CaO). Those oxides are strongly basic and they may be introduced to augment the aldol condensation catalytic ability of the catalyst. It is important to note that those salts are not introduced during the hydrotalcite synthesis and the metal ions are not exchanged into the hydrotalcite structure. As such they are not part of the structure and their amount could be varied independently of the components present in the hydrotalcite structure.

In some embodiments, the addition of the metal salt can be carried out using a complexing or chelating agents. Catalysts using precious metals can have a relatively high cost based on the price of the precious metals. For example, a catalyst using Pd as the alcohol dehydrogenation/hydrogenation component can have both a cost and performance based on the dispersion of the Pd on the support. Due to the high price of such precious metals, reducing the amount of Pd (or other precious metal such as Ru, Rh, or Pt) even slightly can significantly reduce the cost of the catalyst. One way to achieve this without sacrificing catalyst performance is to increase the dispersion of the metal on the supporting material (e.g., the solid base catalyst such as the decomposed hydrotalcite).

The preparation of a supported metal catalyst typically involves a wetness impregnation of the catalyst support material with an aqueous solution of a metal (e.g., palladium, etc.) salt. It is difficult to get high dispersion of such metals when using a basic solid catalyst as the support because the metal ions in the aqueous solution can hydrolyze on the surface of the basic catalyst, and as a result, not enter the pores in the support structure. This leads to metal aggregation on the surface of the support particle (or pellet) and lower metal dispersion overall.

In order to eliminate the hydrolysis of the metal (e.g., Pd(II), etc.) ions on the surface of the basic catalyst component, a chelating agent (e.g., ethylenediaminetetraacetic acid (EDTA), etc.) can be added to the aqueous salt solution during the impregnation of the basic catalyst component. The chelating agent prevents reaction between at least a portion of the metal ions and the basic catalyst, allowing for better metal dispersion due to the metal salt penetrating into the pore structure of the metal oxide component. This improved distribution may be achieved by a variety of different complex forming compounds. These compounds may be negatively charged (such as EDTA, nitrilotriacetic acid, bromide, chloride, etc.), or neutral such as ammonia, ethylenediamine, and crown ethers. The different chelating ions also influence the faceting of the metal crystallites that form on the support surface by changing the location of the sites on the decomposed hydrotalcite where the metal complex adsorption occurs, the local concertation of metal, as well as the decomposition temperature of the metal complex. As a result, different chelating agents may provide differences in performance for otherwise identical chemical compositions. The use of the complexing or chelating agent with the metal salt can be performed prior to or after decomposition of the catalyst material.

In an embodiment, the preparation process can comprise combining a metal salt used with the catalyst with a complexing or chelating agent. The chelating agent can be provided in a molar ratio of moles of complexing agent to moles of metal ions of between about 0.5:1 to about 3:1, or between about 1:1 to about 1:2.5. The mixture of the chelating agent and the metal salt can be mixed until the metal-chelating agent complex forms, and then this solution can be mixed with the catalyst material (e.g., prior to decomposition or after decomposition). The decomposed catalyst can be uniformly coated with the complex solution to a damp solid consistency (incipient wetting process). The damp solid can then be dried, and optionally calcined, prior to being cooled to ambient temperature.

The resulting catalyst prepared using a complexing or chelating agent with the metal salt solution can result in an improved usage of the metal due to the increased area of the metal available for reaction. The improved usage of the metal can improve conversion of ethanol of n-butanol and higher alcohols (as conversion is defined in more detail herein) up to about 30%. In some embodiments, between about 70% to about 95% of the metal can form active catalyst sites, thereby allowing for increased usage of the metal loaded onto the support.

As described herein, the catalyst can be thermally decomposed at a number of points in the catalyst preparation process (e.g., prior to loading with the metal, after loading with the metal, etc.). In preparing hydrotalcite-based versions of the catalyst, a calcination can be performed to decompose the hydrotalcite prior to impregnation with a metal salt solution. A second calcination can also be performed (but may be skipped in favor of chemical reduction of the metal) after the metal impregnation to decompose the metal complexes added to the hydrotalcite. The temperature of these calcinations can have a significant impact on the performance of the catalyst.

Hydrotalcite is known to decompose with structural changes when treated at temperatures above 350° C. However, the decomposed hydrotalcite structure reverts back to the double layered hydroxide structure of the thermally untreated hydrotalcite when exposed to carbon dioxide and moisture in the air. The degree of this reversibility is generally inversely correlated with the calcination temperature of the decomposition. As the temperature of the calcination increases, the resulting structure of the decomposed hydrotalcite becomes less similar to the initial structure and at certain point loses its ability to revert back to the initial structure. At sufficiently high temperatures, the porous structure of the decomposed hydrotalcite collapses and the material no longer naturally returns to the hydrotalcite form when exposed to the ambient atmosphere. Such a collapsed structure is expected to have low surface area and little to no catalytic activity.

Due to the changing structure of the decomposed hydrotalcite at different temperatures, the strength, number, and distribution of the basic active catalyst centers on the decomposed hydrotalcite also changes. This results in an optimal temperature to improve or maximize the reactivity of the hydrotalcite towards aldol condensation functionality.

As mentioned above, the preparation of hydrotalcite-based catalysts may involve two calcination steps. The purpose of the first calcination is to decompose the hydrotalcite. Partially decomposing the hydrotalcite leads to a less hydrophobic material that readily absorbs the aqueous impregnation liquid used to provide the metal. This first calcination temperature could be used to tune catalyst performance by decomposition at a temperature at which the optimal number and distribution of catalytic centers form. The first calcination can also significantly increase the specific surface area of the hydrotalcite, which allows higher loading and better distribution (e.g. a typical hydrotalcite has a surface area of about 5-25 m$^2$/g, which after calcination grows to about 160-220 m$^2$/g).

A second calcination can also be performed after impregnation of the metal, which can be used to change the hydrotalcite structure. In such an embodiment, a partially decomposed hydrotalcite calcined at 475° C. could be impregnated with a metal salt solution, dried, and then calcined at a higher temperature (for example 700° C.) to prepare a more active catalyst than if both calcinations were performed at 475° C., as shown in Example 9. In some embodiments, the conversion of ethanol can be increased as the calcination is performed at a temperature between about 300° C. to about 800° C., or between about 600° C. and about 700° C. When multiple calcination steps are carried out (e.g., at least one prior to metal impregnation, at least one after metal impregnation, etc.), the calcination temperature prior to metal impregnation can be carried out at a temperature between about 350° C. to about 800° C., and the calcination temperature after the metal impregnation can be carried out at a temperature between about 300° C. to about 800° C., where the calcination is carried out in a range of 600° C. to about 700° C. during at least one of the calcination steps.

The resulting catalyst prepared as described herein has an improved performance both in terms of conversion and/or selectivity to higher alcohols. The difference in performance suggests that the catalytic materials have different microstructures that enable the significantly higher performance. It is likely that the coarser dispersion of the hydrogenation metal component or the fact that the dehydrogenation component is accessible by the reactant (the hydrogenation component is not buried in the decomposed hydrotalcite particles) allows for the catalyst component to achieve better performance. In an embodiment, the catalyst can comprise meixnerite (Mg$_6$Al$_2$(OH)$_{18}$·4H$_2$O), and the catalyst can be used alone or in combination with additional materials such as a magnesium aluminum spinel (e.g., MgAl$_2$O$_4$).

The resulting catalyst can include a powder that can be further processed for use in an alcohol conversion process. In an embodiment, a catalyst binder can be added to the catalyst to impart additional mechanical strength. For example, the resulting catalyst can be stirred into a colloidal suspension of silica or alumina in water. The resulting slurry can be extruded into pellets, granules, or other shapes, followed by heating at about 80-130° C. to dryness, and then calcined at temperatures between 300-1000° C.

The catalyst material composed of thermally decomposed hydrotalcite (and/or decomposed hydrocalumite) containing optional alkaline earth metal and dehydrogenation component (e.g., palladium, etc.) can be extruded into commercially applicable size and shape granules without the addition of support.

The catalyst can be prepared in different ways such as extrusion of the thermally decomposed hydrotalcite and/or decomposed hydrocalumite (with or without the optional alkali earth component) followed by loading the dehydrogenation component (e.g. Pd, etc.). Alternatively, the catalyst can be fully prepared as powder, including the deposition of the dehydrogenation component prior to extrusion. Despite the nearly identical composition by these two methods of preparation, the performance can be different due to different spatial distribution of the basic aldol condensation component and the dehydrogenation component (e.g., depositing the Pd after extrusion results in Pd aggregating on the pellet surface).

The resulting catalyst can be characterized in several ways. The catalyst can have a surface area of greater than about 20 m$^2$/g, greater than about 30 m$^2$/g, greater than about 40 m$^2$/g, or greater than about 50 m$^2$/g. In some embodiments, the surface area may be less than about 100 m$^2$/g, or less than about 90 m$^2$/g, or less than about 80 m$^2$/g. The surface area may be at least about 2, at least about 4, at least about 6, at least about 8, or at least about 10 times greater than the surface area of the starting synthetic or natural hydrotalcite, hydrocalumite, or both as applicable. The catalyst can have a pore volume of greater than about 0.05 cm$^3$/g, greater than about 0.1 cm$^3$/g, greater than about 0.2 cm$^3$/g, or greater than about 0.3 cm$^3$/g. In some embodiments, the pore volume may be less than about 0.4 cm$^3$/g, or less than about 0.35 cm$^3$/g. The pore volume may be at least about 2, at least about 4, at least about 6, at least about 8, or at least about 10 times greater than the pore volume of the starting synthetic or natural hydrotalcite. The surface area and the pore volumes may have any range between any lower values and any upper values. In some embodiments, the decomposition of the synthetic or natural hydrotalcite can form an amorphous mixture of aluminum and magnesium oxides, which at higher temperature can form meixnerite (Mg$_6$Al$_2$(OH)$_{18}$·4H$_2$O). The catalyst may also comprise a magnesium aluminum spinel (e.g., MgAl$_2$O$_4$)

While described as a single catalyst, the catalytic function can be obtained, in some embodiments, with a mixture of catalyst components. For example, a physical mixture of single purpose catalysts can be prepared to effectively create a dual-function catalyst system. In this embodiment, a catalyst (or catalysts) for alcohol dehydrogenation/aldehyde hydrogenation would be physically mixed with a catalyst (or catalysts) for aldol condensation. The use of a physical mixture may allow for use of less expensive base metals (Cu, Ni) as the preferred composition of the dehydrogenation/hydrogenation component of the catalyst instead of expensive noble-group metals.

Examples of the single purpose alcohol dehydrogenation/aldehyde hydrogenation catalyst include Cu, Ni, Pd, Ru, Pt, Cr$_2$O$_3$, CuCr$_2$O$_5$, Rh, Co, Fe, Ir, Os or any other commonly used heterogeneous hydrogenation catalyst supported on silica, silica-alumina, alumina, or activated carbon. These catalysts can be prepared via wetness impregnation of the support with an appropriate amount of the metal precursor salt in either an aqueous or other appropriate organic solution. The impregnated support would then be dried and calcined in air at temperatures between about 300° C. and about 550° C.

The aldol condensation catalyst component for the physical mixture can include the hydrotalcite materials (and/or the hydrocalumite materials) described above but without the addition of Pd or Cu salts. For example, aldol condensation catalyst component can comprise any of the decomposed hydrotalcite materials described herein. The hydrotalcite may be treated with an alkaline or alkaline earth oxide and thermally decomposed as described above.

In some embodiments, the catalyst can comprise one or more materials in place of the decomposed hydrotalcite. For example, the catalyst can comprise a magnesium aluminum spinel (e.g., MgAl$_2$O$_4$). The magnesium aluminum spinel can be treated with any of the additional components described above (e.g., having alkaline metal oxide such as MgO/CaO or Pd, Cu, etc. on MgAl$_2$O$_4$). In addition, the pelletization of the spinel materials can be done as described above for hydrotalcite. Extrusion can be done both prior to the deposition of the dehydrogenation component or after. The resulting catalyst can then be used in the production of n-butanol.

The catalysts described herein can be used with a number of processes to convert an alcohol to one or more higher alcohols. In general, the conversion process comprises contacting a reactant comprising an alcohol with the catalyst described herein at a reaction temperature and pressure sufficient to produce a reaction product. The reactor can include any suitable type of reactor such as a batch reactor, plug flow reactor, continuous stirred tank reactor, contact column, reactive distillation tower, or the like. The reaction can occur in the gas and/or liquid phase within the reactor. In some embodiments, the reactor containing the catalyst described herein can be used to convert ethanol to butanol or another higher alcohol (e.g., $C_5$-$C_{13}$ alcohols, or higher alcohols).

In some embodiments, the catalyst(s) described herein can produce higher alcohol conversion products that can serve as catalyst inhibitors. The higher alcohol catalysts produce several byproducts in small amounts, such as esters, ethers, alkanes, and aldehydes. Depending on the process configuration of the reactor system, some of these byproducts may be recycled back to the reactor system and passed over the catalyst again in order to optimize the process economics. For example, aldehydes in particular can be recycled as they are intermediates in the reaction to form longer chain alcohols. While ethers, alkanes, and aldehydes proved to have no or slight beneficial impact on catalyst performance, the esters appear to act as catalyst inhibitors, even at low concentrations. Therefore, any recycle configurations for mixing unreacted ethanol from the reactor effluent back into the reactor feed should include a purification step to remove most or all of the esters formed during the reaction. Based on testing, the effects of the esters on the catalyst performance appears to be reversible, and as a result, should any esters be present in the feed to the reactor, the reduction in conversion efficiency can be corrected by improving the removal of the esters from the feed.

In some embodiments, the catalyst(s) described herein can be used with a reactive distillation system. In chemical processing, chemical reaction and the purification of the desired products by distillation may be carried out sequentially. The performance of this chemical process structure may be improved by the integration of reaction and distillation in a single multifunctional process system or unit. This integration concept is called "reactive distillation." The reaction may occur within the same vessel, or a second vessel in fluid communication with a separation vessel may be considered a reactive distillation. For example, a side reactor carrying out a reaction that is in fluid communication with a distillation column that removes at least a portion of the products would be considered a reactive distillation process. As advantages of this integration, chemical equilibrium limitations may be overcome, higher selectivities may be achieved, the heat of reaction may be used in situ for distillation, auxiliary solvents may be avoided, azeotropic and/or closely boiling mixtures may be more easily separated, or any combination thereof. Increased process efficiency and reduction in overall capital costs may result from the use of this approach.

A reactive distillation system comprises at least one separator (e.g., a distillation tower) in which a reaction is occurring and/or coupled to a vessel in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, pressure control elements, or any combination thereof. Such columns may also employ some combination of reflux condensers and/or reboilers, including intermediate stage condensers and reboilers. In an embodiment, the reactive distillation system described herein may comprise a distillation tower.

As indicated above, the catalyst(s) described herein can be used in systems and methods for the production of higher alcohols from ethanol. The present disclosure further provides improved processes for the production of one or more high purity higher alcohols from a lighter alcohol feed or from a feedstock comprising a major proportion of a lighter alcohol feed and a minor proportion of impurities such as iso-propanol, iso-butanol, water, or any combination thereof. While not commonly present in alcohol feed streams, impurities that can poison the particular catalyst used should be limited, avoided and/or removed. For example, sulfur or nitrogen heterocyclic compounds can frequently act as catalyst poisons and, if present, should be removed before introducing the alcohol feed stream to the reactive distillation column.

With respect to the alcohol forming the reactant in the formation process, the present description is generally described in terms of ethanol. However, a number of alcohols can form the reactant. In some embodiments, the process is believed to occur with a feed comprising any alcohol comprising an alpha hydrogen in regard to the hydroxyl group (e.g., an alpha hydrogen alcohol) including, but not limited to, a primary or secondary alcohol. In an embodiment, the feed may comprise one or more alcohols other than methanol and may include any $C_2$-$C_5$ alpha hydrogen alcohols. In addition to ethanol, additional alcohols can be used in the reaction feed including, but not limited to, propanol, isopropanol, butanol, isobutanol, pentanol, etc.

The present systems and methods provide a reactive distillation system in which an alcohol feed comprising an alcohol having an alpha hydrogen is fed to a reactive distillation system. In an embodiment, ethanol may be the sole or primary component of the feed. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction.

The single feed may comprise a single reactant such as an alpha hydrogen alcohol (e.g., ethanol). A "single alcohol feed" refers to a feed stream of a single alpha hydrogen alcohol, and a "single ethanol feed" refers to a single feed stream in which ethanol is the sole or at least the primary constituent. In contrast, the term "dual feed" in the context of a distillation column refers to two separate chemical feed streams. For example, in some of the present embodiments, dual feeds can include an ethanol feed stream and a separate hydrogen feed stream. The term "reactive distillation system" is used conventionally to refer to a distillation column in which separation is performed while a reaction is occurring. The reaction may occur within the same distillation column and/or within a second vessel in fluid communication with a distillation column may still be considered a reactive distillation column. For example, a side reactor carrying out a reaction that is in fluid communication with a distillation column that removes at least a portion of the products would be considered a reactive distillation process occurring in a reactive distillation system.

In general, higher alcohols are produced by the addition of one or more lighter alcohols and/or side products. In embodiments where the production of n-butanol is desired, the primary and desired reaction is the conversion of two ethanol molecules to one butanol molecule with release of one water molecule. To this end, the present application provides systems and methods for the production of higher alcohols from an alpha hydrogen alcohol such as ethanol, which includes reacting one or more alpha hydrogen alcohols over the catalyst(s) described herein in a reactive distillation system, thereby producing higher alcohols and water. To this end, the present application provides catalysts along with systems and methods for the production of higher alcohols from an alpha hydrogen alcohol, which includes reacting one or more alpha hydrogen alcohols over the catalyst(s) in a reactive distillation system, thereby producing one or more higher alcohols, and water. In some embodiments byproducts may also be produced as described in more detail herein.

In an embodiment, a single reactive distillation column is used. Water can be removed (e.g., continuously) from the top of the reactive distillation column as an overhead stream. In some embodiments, the overhead stream may comprise some amount of the alpha hydrogen alcohol(s) present in the feed such as ethanol. Higher alcohols can be removed (e.g., continuously) from the bottom of the column as a bottoms stream. Optionally, contaminating byproducts present following reaction of the alpha hydrogen alcohol(s) over the conversion catalyst can be reacted over a suitable hydrogenating catalyst in the lower part of the column or in a separate hydrogenation reactor. The hydrogenation can convert difficult to separate byproducts into species which are easier to separate from the higher alcohol(s). Consequently, the process can also include purifying the higher alcohols, including separating one or more higher alcohols, by distilling out resulting hydrogenated byproducts.

In its simplest form, a reactive distillation system may comprise a reactor vessel operating with a liquid and/or gas phase reaction in which water and any unreacted alpha hydrogen alcohols are removed as the overhead product and a reaction product is removed as the bottoms product. The reactor vessel can comprise a continuous stirred-tank reactor (CSTR). Alternatively, such a system may comprise a batch reactor in which water and any unreacted alpha hydrogen alcohols are removed during the reaction and the liquid product is removed after completion of the reaction to a desired degree of conversion.

In an embodiment, a reactive distillation column with a single feed of an alpha hydrogen alcohol(s) as shown in FIG. 1 can produce byproducts including hydrogen as an overhead stream 10, water as a distillate stream 9, and higher alcohols (e.g., $C_4$-$C_{13}$ alcohols such as n-butanol, or higher alcohols) as a bottoms product stream 15. In general, the alpha hydrogen alcohol feed can comprise any primary alcohol other than methanol and may include any $C_2$-$C_5$ alpha hydrogen alcohols. In an embodiment, the alpha hydrogen alcohol feed stream 4 can comprise ethanol, butanol, and/or propanol. In some embodiments, the alpha hydrogen alcohol feed stream may comprise ethanol as the only alpha hydrogen alcohol. The alpha hydrogen alcohol is fed as a feed stream 4 to the reactive distillation column 1. The column reflux and reboil ratios are maintained such that high recovery of higher alcohols is obtained in the bottoms stream 15. The higher alcohols and by-products are produced due to the reaction over the catalyst 7. The catalyst(s) 7 may include any of the catalysts described or referenced above. The reactants and products may flow through the reactor/column reacting and flashing along the length of the reactor/column. In some embodiments, the alpha hydrogen alcohol may react in the liquid phase over the catalyst 7 to produce the higher alcohols. The removal of the higher alcohols and the by-products during the distillation may increase the extent of reaction. The column conditions can be controlled to alter or tune the product distribution. For example, the temperature in the reaction zone (e.g., the zone in which the reacts are in contact with the catalyst) and/or the contact time (e.g., as controlled by reflux/reboil ratios, column holdup, etc.) can be controlled to provide a desired higher alcohol product distribution.

Unconverted alpha hydrogen alcohols (e.g., ethanol) in the feed that may be carried with the distillate stream is condensed (e.g., in condenser 6 and separated in flash tank 8) and refluxed back into the column 1. Continuous removal of the higher alcohols and the by-products such as water from the reactive distillation column moves the reaction forward. The higher alcohols and other heavy boiling components leave in the bottoms stream 15 of the reactive distillation column 1. The column 1 can be operated between a pressure of about 1 atm and about 100 atm. The temperature profile in the column 1 is dictated by the mixture's boiling point along the height of the column. High conversion of the alpha hydrogen alcohol feed to products can be achieved by the counter-current flow of reactants and products in addition to overcoming the reaction equilibrium by removal of products. The bottoms product stream 15 can be separated to provide a stream comprising predominantly lighter alcohols (e.g., $C_2$-$C_4$ alcohols) and a stream comprising predominantly higher alcohols. The higher alcohols stream may be purified to comprise greater than about 90%, greater than about 95%, greater than about 98%, greater than about 99%, or greater than about 99.5% pure higher alcohols. The number of stages (or HETP in case of a packed column) for the column 1 can range from about 2 to about 100. The lighter alcohols stream can be removed as a separate product stream and/or recycled to the feed stream 4 for further reaction within the column 1.

While illustrated as having the catalyst 7 disposed within the central portion of the column 1, the catalyst 7 may be located only above or below the alpha hydrogen alcohol feed location. In an embodiment, the catalyst 7 may be disposed only above the feed location, and the lower portion of the column may comprise trays, packing, or the like to provide a stripping section. In some embodiments, the catalyst 7 may be disposed only below the feed location, and the upper portion of the column may comprise trays, packing, or the like to provide a rectifying section.

Figure 2:
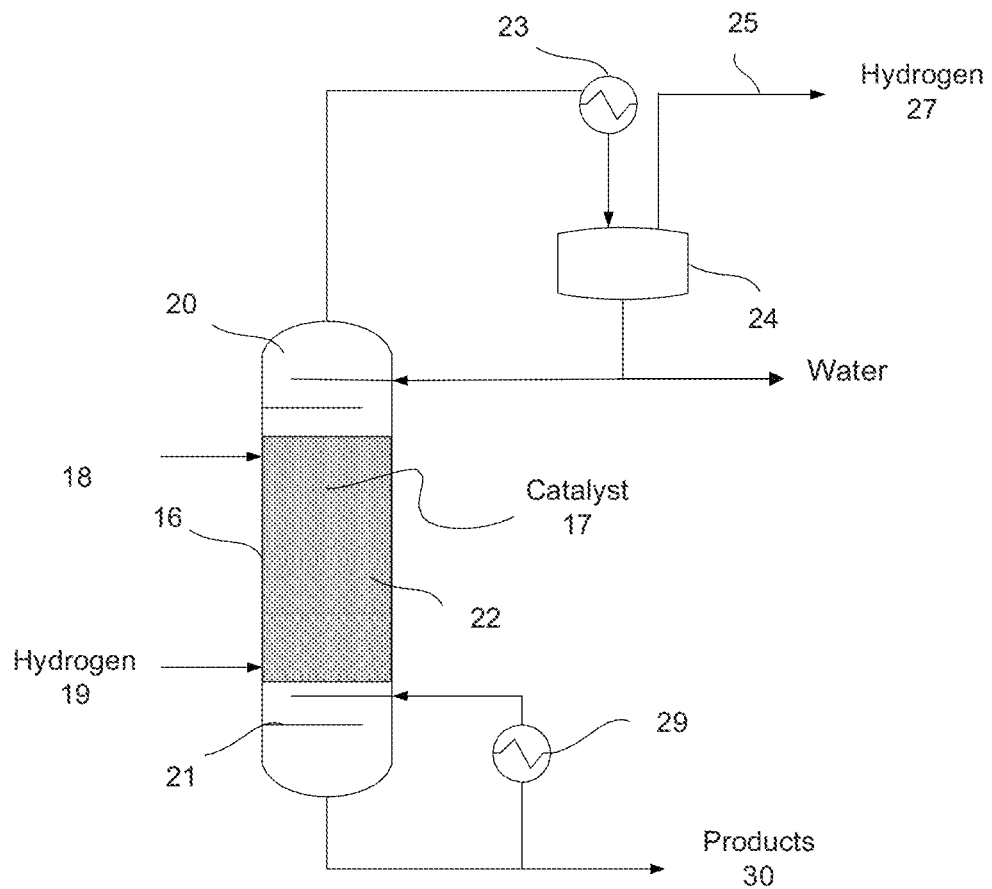
FIG. 2 shows another simplified schematic of a reactive distillation system according to still another embodiment.

FIG. 2 shows a process schematic for a reactive distillation column 16 with dual feed (alpha hydrogen alcohol feed 18 and hydrogen feed 19). The alpha hydrogen alcohol feed 18 is fed to the upper part of the column 16 (upper feed 18). Hydrogen is fed to the lower part of the column (lower feed 19). Due to boiling point difference, hydrogen moves towards the top of the column 16 and the alpha hydrogen alcohol moves towards the bottom of the column 16, thereby allowing the alpha hydrogen alcohol to react over the catalyst 17 in the column 16 in the presence of hydrogen. The excess hydrogen may cause the intermediate aldehydes to be hydrogenated more readily, potentially allowing for more selectivity to the shorter alcohols, such as 1-butanol. Conversion of the alpha hydrogen alcohols may or may not be affected by the addition of hydrogen to the reactor feed. In a reactive distillation the addition of hydrogen could occur at the very bottom of the column or anywhere along the length of the column where the reactive catalyst and/or packing is located. The reactive distillation column 16 may be operated between a pressure of about 1 atm and about 100 atm. The reactive distillation column 16 may otherwise be the same or similar to the reactive distillation column of FIG. 1.

Figure 3:
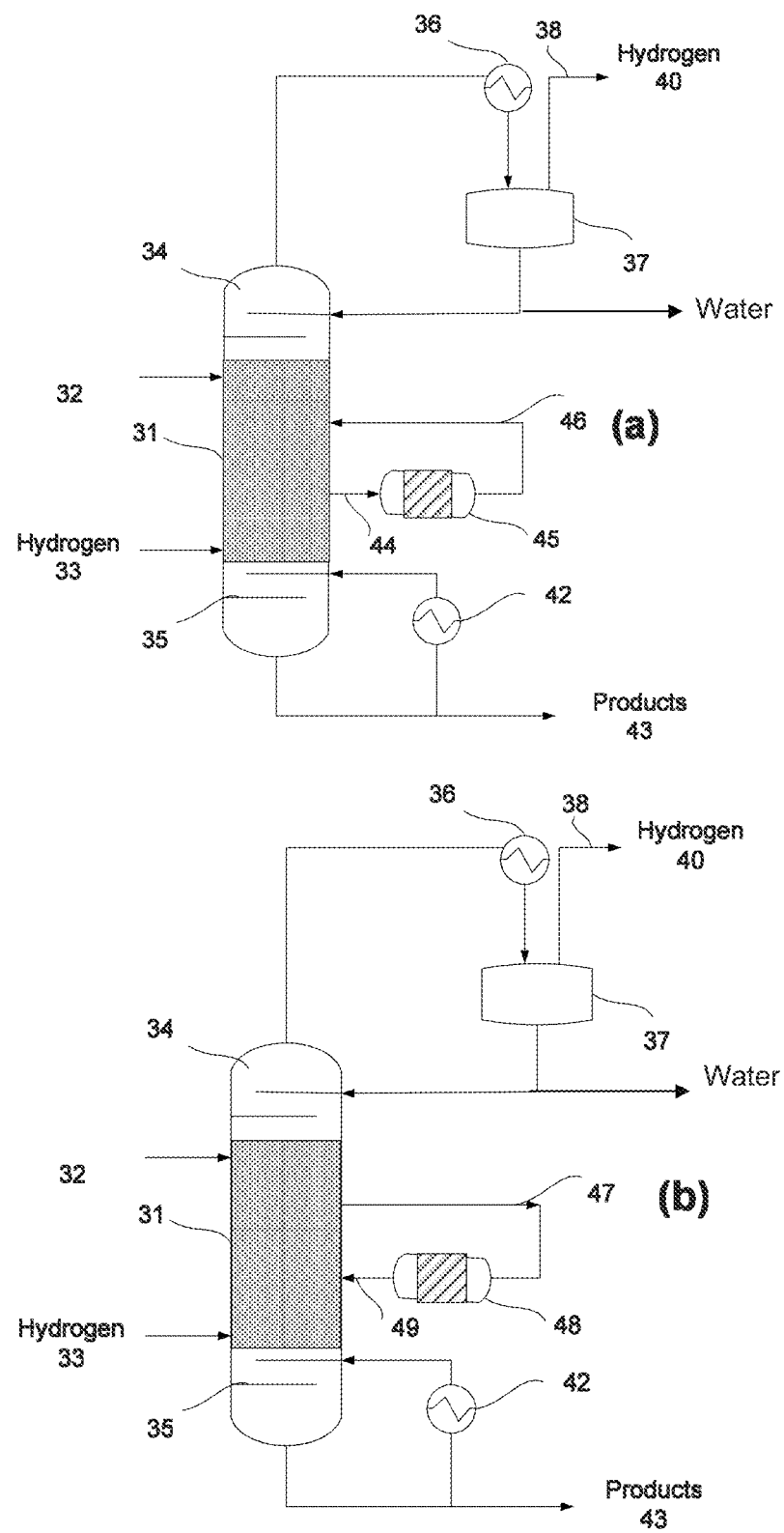
FIGS. 3(a) and 3(b) shows a simplified schematic of a reactive distillation system according to yet another embodiment.

FIG. 3 (a) shows a process schematic for a reactive distillation column 31 with dual feed (alpha hydrogen alcohol feed 32 and hydrogen feed 33). While dual feeds are illustrated, a single feed may be used, such as a single feed of an alpha hydrogen alcohol. One or more side reactors, such as side reactor 45, can be utilized to increase the amount of residence time available for the reaction. As illustrated, the side reactor 45 can comprise a catalyst as described herein. Stream 44 can be in the gas phase and react over the catalyst in side reactor 45. FIG. 3 (b) shows a process schematic for a reactive distillation column 31 with dual feed (alpha hydrogen alcohol feed 32 and hydrogen feed 33). A side reactor 48 can be utilized to increase the amount of residence time available for the reaction. Stream 47 is in liquid phase and can react over the catalyst in side reactor 48 (e.g., the liquid reacts in the liquid phase over the catalyst). In some embodiments, catalyst can be present only in the side reactor or in the side reactor and the column. In some embodiments, the catalyst may be present in only the side reactor, and the column may not comprise a catalyst.

In some embodiments, one or more of the feeds (e.g., alpha hydrogen alcohol feed 32 and hydrogen feed 33) could be introduced directly into the side reactors prior to entering the distillation column. For example, the alpha hydrogen alcohol feed 32 could enter the side reactor or be combined with the stream from the column prior to entering the side reactor. This may be useful in embodiments in which the distillation column does not comprise a catalyst.

Figure 4:
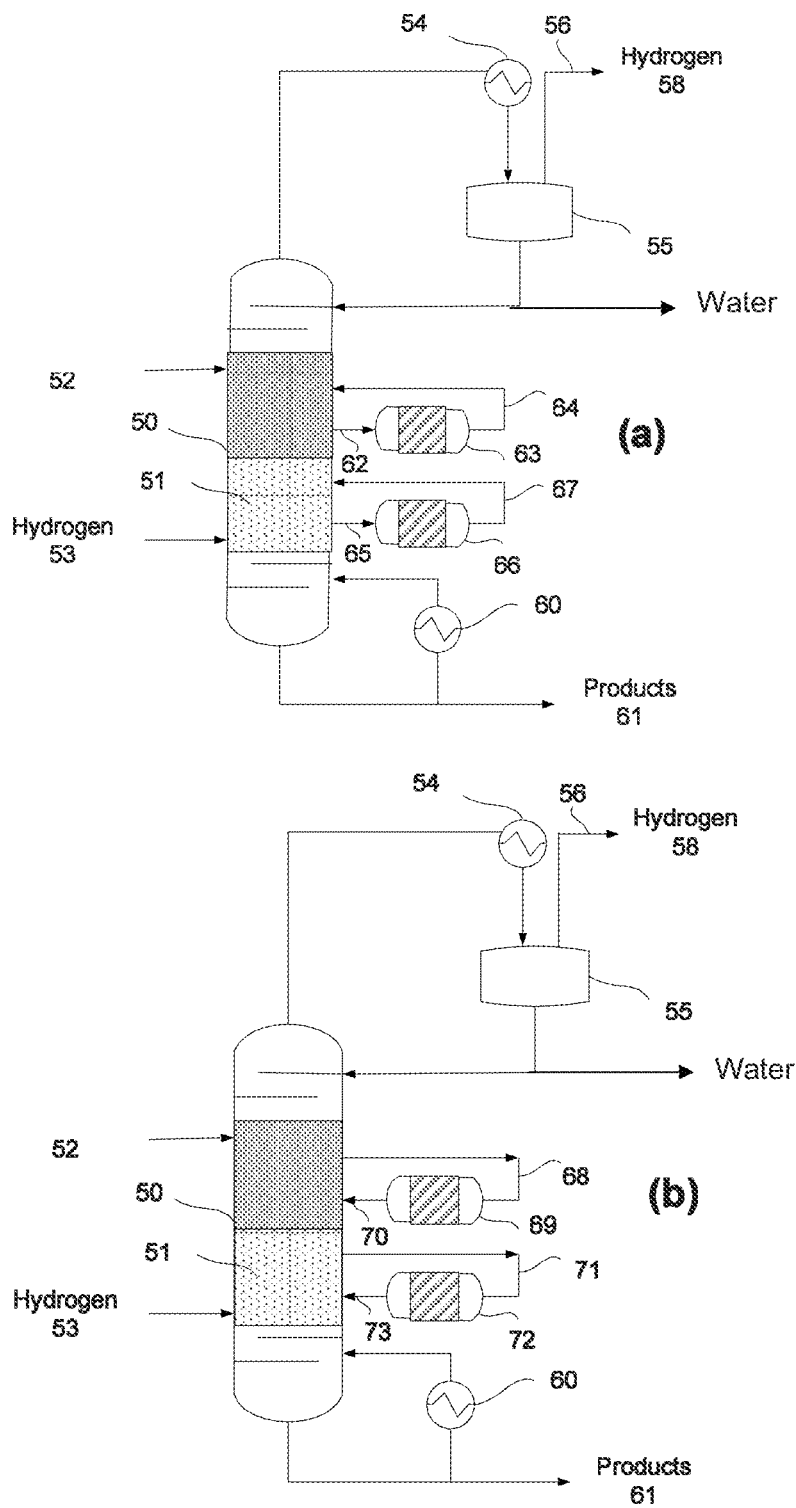
FIGS. 4(a) and 4(b) shows a simplified schematic of a reactive distillation system according to still another embodiment.

FIG. 4 (a) shows a process schematic for a reactive distillation column with dual feed (alpha hydrogen alcohol and hydrogen). While dual feeds are shown in FIG. 4(a), only a single feed of an alpha hydrogen alcohol may be present. Multiple side reactors can be utilized to increase the amount of residence time available for the reaction. Feed streams represented by 62 and 65 are in the gas phase and react over the catalyst (e.g., any of the catalysts described herein) in side reactors represented by 63 and 66. FIG. 4(b) shows a process schematic for a reactive distillation column with dual feed (alpha hydrogen alcohol and hydrogen). Multiple side reactors can be utilized to increase the amount of residence time available for the reaction. Streams represented by 68 and 71 can be in the liquid phase and react over the catalyst in side reactors represented by 69 and 72. A plurality of side reactors can be used in the configurations shown in FIG. 4. In some embodiments, the catalyst can be present only in the side reactor, and the column may not comprise a catalyst.

As illustrated in FIG. 4(a) and FIG. 4(b), the column 50 may comprise two catalysts. For example, two different catalysts may be present in the column. The catalysts may comprise the same or different components. Similarly, when a plurality of side reactors are present, the catalysts in each side reactor may be the same or different. The different reaction conditions in the different portions of the column and the different side reactors may be taken into account when determining the catalyst or catalysts to include in each area. In some embodiments, the catalysts used in the column and/or the side reactors may be the same.

As a general proposition, the number of side reactors and the type of catalyst with which the column and each side reactor are individually charged can be selected to accommodate a desired variety of feedstocks, a desired range of product compositions, or a combination thereof during operation of the reactive distillation column. During continuous operation, the flow rates between the side reactors and the column can be adjusted (e.g., selectively tuned) to respond to changes in feedstock, to achieve a desired product composition, or a combination thereof. The ability to adjust the flow rates between the side reactors and the column advantageously allows feedstocks to be changed when market fluctuations in price and availability favor the use of a feedstock having a different composition (e.g. lower quality, higher water content, different mix of alpha hydrogen alcohols, etc.). The ability to adjust the flow rates between the side reactors and the column advantageously allows feed quality to be maintained despite fluctuations in feedstock composition during continuous operation. The ability to adjust and/or control the flow rates between the side reactors and the column may also allow for the reduction or elimination of undesirable byproducts to advantageously increase the purity of the desired products. In some embodiments, the catalyst(s) may only be present in the side reactors and not in the distillation column.

As noted above, one or more of the feeds (e.g., alpha hydrogen alcohol feed 52 and hydrogen feed 53) could be introduced directly into the side reactors prior to entering the distillation column. For example, the alpha hydrogen alcohol feed 52 could enter the side reactor or be combined with the stream from the column prior to entering the side reactor. This may be useful in embodiments in which the distillation column does not comprise a catalyst.

Figure 5:
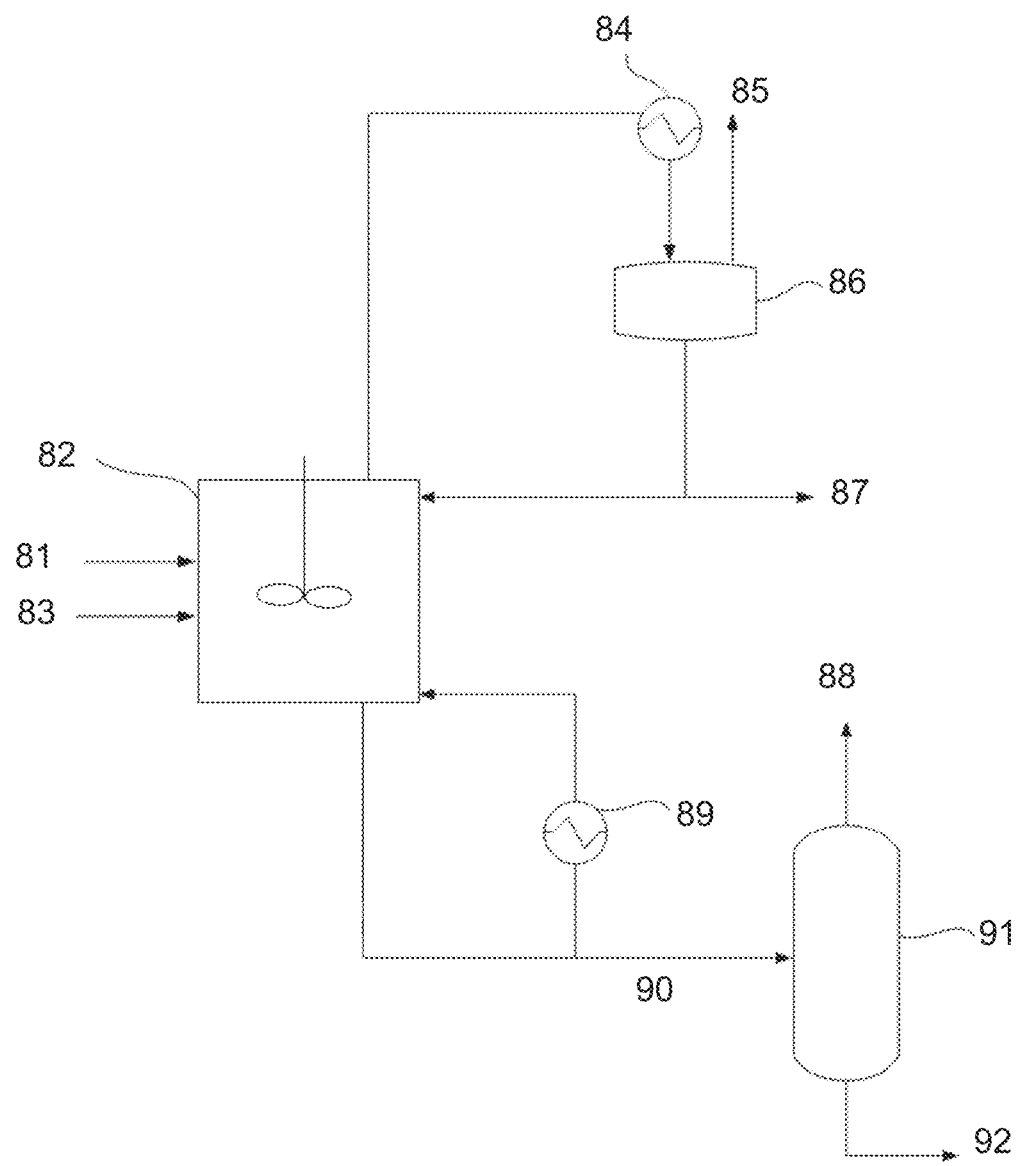
FIG. 5 shows a simplified schematic of a reactive distillation system according to an embodiment.

Another embodiment of a system for producing higher alcohols is shown in FIG. 5. In this embodiment, the reactive distillation system may comprise a continuous stirred-tank reactor (CSTR) 82, which can comprise a catalyst as described herein, that is coupled to a phase separator 91 and configured for the dehydration of an alpha hydrogen alcohol with the formation of one or more higher alcohols. In an embodiment, production of higher alcohols may be accomplished by passing the feed stream 81, which comprises a feed of an alpha hydrogen alcohol or an alpha hydrogen alcohol and optionally hydrogen in stream 83, into the CSTR 82 wherein the feed mixes and contacts the catalyst under conditions where higher alcohols and water are formed. As the conversions proceed, the resulting mixture may pass to a phase separator 91 from which the water leaves as distillate 88 and higher alcohols including any butanol or heavier alcohols can leave as a bottom product 92. Phase separator 91 may be any phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns.

Figure 6:
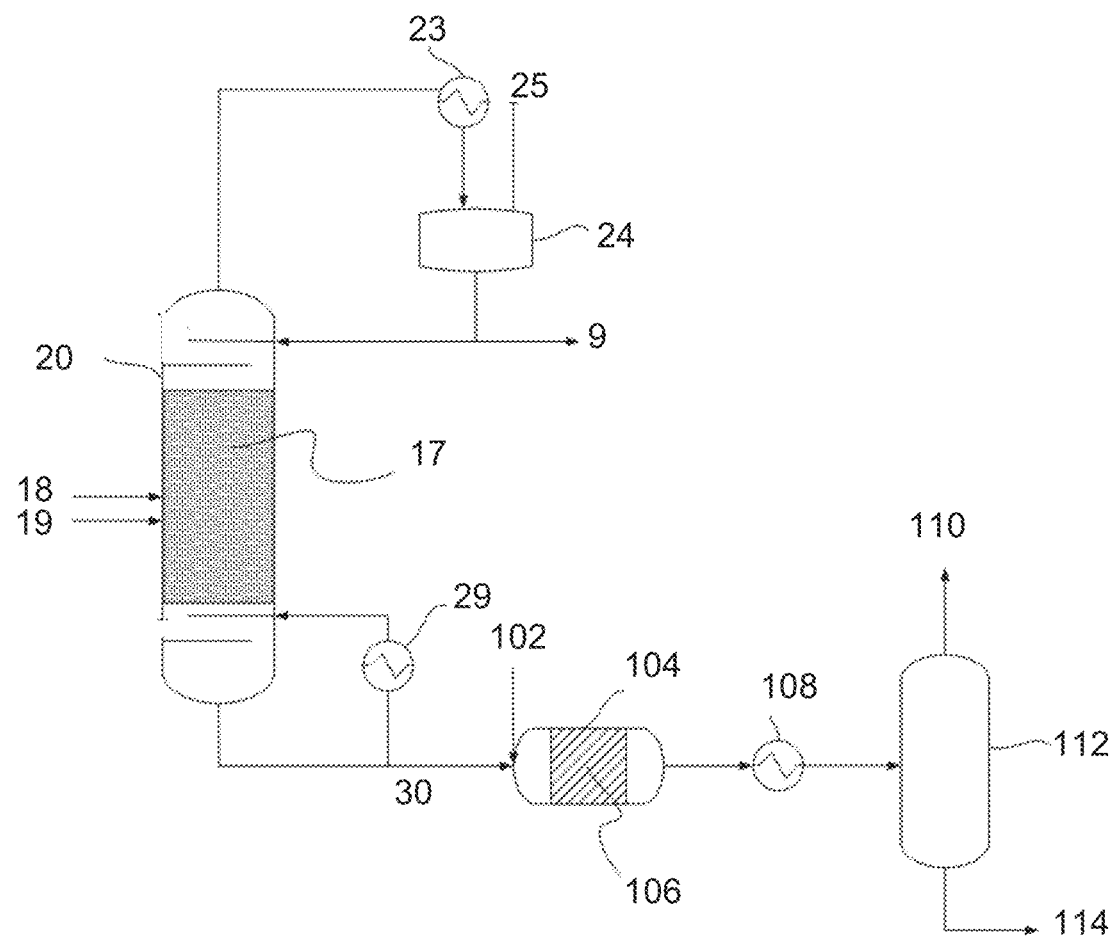
FIG. 6 shows a simplified schematic of a reactive distillation system according to another embodiment.

FIG. 6 shows a process schematic where the bottoms product 30 from the reactive distillation column 20 illustrated in FIG. 2 is sent to a hydrogenation reactor 104 comprising a hydrogenating catalyst 106 with a hydrogen co-feed in stream 102. Suitable hydrogenating catalyst(s) may comprise various components and are described in more detail herein. At least a portion of the byproducts can be hydrogenated in the hydrogenation reactor 104, pass through heat exchanger 108, and can then be separated using a separator 112. The separator 112 may comprise any of the types of separators described herein with respect to the reactive distillation system. Alternatively or in addition to the separators already described, the separator 112 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. The separator 112 also may be any other type of separator, such as a membrane separator. In a specific embodiment, the separator is a knockout drum. Finally, the separator may be any combination of the aforementioned separators arranged in series, in parallel, or combinations thereof. In an embodiment, separator 112 comprises a distillation column. The outlet of the hydrogenation reactor 104 may be passed through a heat exchanger 108 (e.g., a condenser) and cooled before entering the separator 112. The heat exchanger 108 may be any equipment suitable for heating or cooling one stream using another stream. Generally, the heat exchanger 108 is a relatively simple device that allows heat to be exchanged between two fluids without the fluids directly contacting each other. Examples of suitable heat exchangers 108 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 114 from the separator 112 may comprise one or more higher alcohols (e.g., butanols, pentanols, etc.) and may have a purity of greater than about 90%, greater than about 95%, greater than about 96%, greater than about 97%, greater than about 98%, greater than about 99%, or greater than about 99.5% by weight. Unconverted water and the hydrogenated byproducts may be removed as an overhead product 110, and may be used, for example, as fuel or a feed to one or more processes. In an embodiment, the separator 112 may be operated between a pressure of 1 atm and 80 atm.

In an embodiment, the bottoms product stream 114 may pass to another separator. The separator may then separate the bottoms product stream into a higher alcohols stream and a byproduct stream comprising one or more heavier hydrogenation products produced in the hydrogenation reactor 104. The components within a mixed higher alcohols stream can be further separated to produce one or more product streams comprising predominately individual higher alcohols. This separation scheme may allow for one or more resulting higher alcohol streams to have individual component purities of greater than about 90%, greater than about 95%, greater than about 96%, greater than about 97%, greater than about 98%, greater than about 99%, or greater than about 99.5% of the respective higher alcohol by weight. In an embodiment, the product stream may have a purity of greater than about 90%, greater than about 95%, greater than about 96%, greater than about 97%, greater than about 98%, greater than about 99%, or greater than about 99.5% n-butanol by weight.

Figure 7:
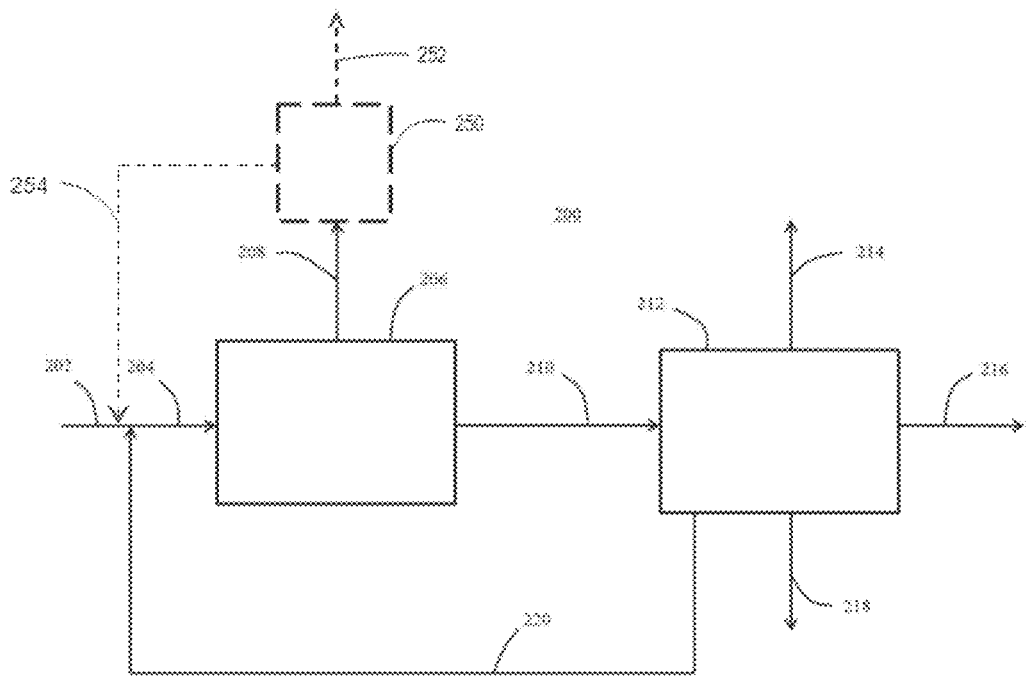
FIG. 7 illustrates a schematic flow diagram of a reactive distillation system with a recycle according to an embodiment.

As schematically illustrated in FIG. 7, a higher alcohols production process may comprise a products separation section 212 for use in separating the product stream and allowing at least a portion of any unreacted ethanol to be recycled to the inlet of the process. The products separation section may be configured to provide at least one product stream comprising a single reaction product such as a higher alcohol (e.g., propanol, butanol, hexanol, etc.), or another reaction product having a purity of greater than about 90%, greater than about 95%, greater than about 96%, greater than about 97%, greater than about 98%, greater than about 99%, or greater than about 99.5% by weight. In an embodiment, a separation train may be used to produce a plurality of streams that each predominately comprise a single reaction product such as a higher alcohol (e.g., propanol, butanol, hexanol, etc.), or another reaction product having a purity of greater than about 90%, greater than about 95%, greater than about 96%, greater than about 97%, greater than about 98%, greater than about 99%, or greater than about 99.5% by weight. At least one additional stream may be produced comprising the remaining components of the product stream from the reactive distillation column. In an embodiment, a plurality of streams are produced in the separation section comprising a stream predominantly comprising butanol, a stream predominantly comprising propanol, a stream predominantly comprising hexanol, a stream comprising water, a stream comprising ethanol, a heavies stream comprising one or more reaction products with boiling points above the boiling point of hexanol, or any combination thereof. In an embodiment, a stream comprising ethanol, if present, may be recycled to the reactive distillation column.

As schematically illustrated in FIG. 7, a system 200 for producing one or more higher alcohols may comprise a feed stream 202 comprising an alpha hydrogen alcohol that may be optionally combined with a recycle stream 220 comprising an alpha hydrogen alcohol to form the inlet stream 204 to the reactive distillation system 206. The system 200 may be useful for embodiments in which there is an incomplete conversion of an alpha hydrogen alcohol in the reactive distillation system 206. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIGS. 1-6 herein. The reactive distillation system 206 may produce an overhead product stream 208 and a bottoms product stream 210. The overhead product stream 208 may comprise water, hydrogen, unreacted alpha hydrogen alcohol(s), or a combination thereof and may generally correspond to any of these streams as illustrated in FIGS. 1-6. Similarly, the bottoms product stream 210 may comprise higher alcohols (e.g., butanol, 1-hexanol, 1-octanol, 2-ethyl-1-butanol, 2-ethyl-1-hexanol, butanediol, etc.), ethyl butyrate, 2-pentanone, propanol, additional reaction products, possibly water, and/or any combination thereof. In an embodiment, the bottoms product stream 210 may correspond to any of these streams as illustrated in FIGS. 1-6.

An optional overhead separation section 250 may receive the overhead product stream 208 from the reactive distillation system 206. The overhead separation section 250 may be configured to separate water from any alpha hydrogen alcohol(s) (e.g., ethanol) in the overhead product stream 208, which may be present at a water-alcohol azeotrope such as a water-ethanol azeotrope, to allow the feed alpha hydrogen alcohol to be recycled to the system while removing the water to drive the reaction within the reactive distillation system 206. The overhead separation section 250 may comprise any number or type of separation units, which may employ pressure- and/or temperature-swing distillation, pressure- and/or temperature-swing adsorption, membrane-based separation, molecular sieve separation, any other suitable separation technology, or any combination thereof, all of which may be used to remove a desired amount of water from the overhead product stream 208. The overhead separation section 250 may produce a recycle stream 254 comprising one or more alpha hydrogen alcohols and an outlet stream 252 comprising water. The recycle stream 254 may comprise the alpha hydrogen alcohol(s) for use as a feed for the reactive distillation system 206. In some embodiments, the alpha hydrogen alcohol stream 254 may not be recycled to the reactive distillation system, but rather may exit the system 200 as a separate product stream. While illustrated as being combined prior to introduction to the reactive distillation system 206, the feed stream 202 and the recycle stream 254 (as well as recycle stream 220) may be fed individually to the reactive distillation system 206.

A products separation section 212 may receive the bottoms product stream 210 from the reactive distillation system 206, and, in some embodiments, the overhead product stream 208. The products separation section 212 may comprise any number or type of separation units, which may employ pressure- and/or temperature-swing distillation, pressure- and/or temperature-swing adsorption, membrane-based separation, cryogenic distillation, any other suitable separation technology, or any combination thereof, all of which may be used to generate a desired product distribution. The products separation section 212 may generally produce one or more product streams such as product stream 216. The higher alcohol product stream 216 may comprise a higher alcohol having a purity of greater than about 90%, greater than about 95%, greater than about 96%, greater than about 97%, greater than about 98%, greater than about 99%, or greater than about 99.5% by weight. In addition to the higher alcohol product stream 216, one or more additional streams may be produced by the products separation section 212. In an embodiment, a lights product stream 214 may be produced. The lights product stream 214 may comprise water, any alpha hydrogen alcohol from the feed, hydrogen, other light components, or any combination thereof. In an embodiment, a heavies product stream 218 may comprise one or more reaction products (e.g., one or more aldehydes, ketones, heavy alcohols, any combination thereof, etc.). In an embodiment, a recycle stream 220 may be produced. The recycle stream may comprise one or more alpha hydrogen alcohols for use as a feed for the reactive distillation system 206. In some embodiments, the alpha hydrogen alcohol(s) stream may not be recycled to the reactive distillation system, but rather may exit the system 200 as a separate product stream. Each of the potential product streams 214, 216, 218, and/or 220 may exit the system as separate product stream and/or exit the system 200 for use as fuel and/or as a feed to additional downstream processes. While illustrated as separate streams 214, 216, 218, and/or 220, one or more of these streams may exit the system 200 as a combined product stream.

The higher alcohols production process may produce a variety of products. For example, the process may produce one or more higher alcohols such as butanol, propanol, 1-hexanol, 1-octanol, 2-ethyl-1-butanol, 2-ethyl-1-hexanol, butanediol, and heavier alcohols. The process may also produce various additional products such as ethyl acetate, butyl acetate, ethyl butyrate, 2-pentanone, propanol, and/or water. Various side products may also be produced that can result in a complex mixture of components that can be difficult to separate. This complex mixture may exhibit a number of binary azeotropes, ternary azeotropes, and possibly azeotropes containing four or more components. Some of the azeotropes can be homogeneous, while others can be heterogeneous. These azeotropes can give rise to distillation boundaries in the composition space that, along with the azeotropes, act as barriers for distillation and limit the ability to achieve high recovery and/or purity of the desired products using distillation alone. When water is present in a sufficient amount, the system may also comprise a multiple liquid phase region, with vapor-liquid-liquid and/or liquid-liquid equilibrium tie-lines that cross some of these boundaries. In some embodiments, a product separation system can exploit this characteristic of the system and comprise a separation sequence comprising distillation columns and decanters. This system may be capable of producing one or more high purity product streams such as one or more high purity higher alcohol stream, an ethyl acetate stream, and potentially one or more other valuable byproduct streams.

In some embodiments, conventional, separate reactors and distillation systems can be used to carry out the reaction steps sequentially. For example, one reactor would be used to selectivity convert ethanol to higher alpha hydrogen alcohols and a second reactor can be used to selectively convert the higher alpha hydrogen alcohols to higher alcohols. The resulting higher alcohols stream can be used for a variety of commercial processes including as precursors to various polymers, industrial solvents, and the like. In some embodiments, the higher alcohols can be further converted to ethers, esters or the like.

In an embodiment, the higher alcohol can comprise butanol, which can be further processed into various fuel components. For example, the higher alcohol product can be contacted, with or without a solvent, with one or more acid catalysts (e.g., sulfuric acid, heteropoly acids, natural clay minerals, cation exchanged resins, metal oxides, mixed metal oxides, metal salts, zeolites, perfluorinated ion-exchanged polymers, ion-exchanged resins, mixtures thereof, etc.) at a temperature between about 50° C. and about 450° C. and at a pressure between about 0.1 MPa and about 21 MPa to produce a reaction product comprising two or more ethers (e.g., dialkyl ethers, etc.). The resulting ethers can be used in various ways including as an additive for a fuel mixture. More details on the conversion of a higher alcohol product comprising butanol to ethers can be found in U.S. Pat. No. 8,398,728 to Ozer et al. and U.S. Patent Application Publication No. 2010/0197974 to Harmer et al., both of which are incorporated by reference herein in its entirety.

For the systems described herein comprising a hydrogenation catalyst or catalysts, the hydrogenating catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys, oxides (e.g., $PtO_2$), or any combination thereof, either alone or with promoters such as W, Mo, Au, Ag, Cr, Zn, Mn, Sn, B, P, Bi, and alloys, oxides (e.g., $Cr_2O_3$, $Cu_2Cr_2O_5$), or any combination thereof. Other effective hydrogenating catalyst materials include either supported nickel or ruthenium modified with rhenium. In an embodiment, the hydrogenating catalyst also includes any one of the supports described below, depending on the desired functionality of the catalyst. The hydrogenating catalysts may be prepared by methods known to those of ordinary skill in the art.

In an embodiment, the hydrogenating catalyst includes a supported Group VIII metal catalyst and a metal sponge material (e.g., a sponge nickel catalyst such as Raney nickel). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 wt % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 wt % remains in the formed sponge nickel catalyst. In another embodiment, the hydrogenating catalyst is prepared using a solution of ruthenium(III) nitrosylnitrate or ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenating catalyst may include a catalyst support to support and stabilize the catalyst. The type of catalyst support used depends on the chosen catalyst and the reaction conditions. Suitable supports may include, but are not limited to, carbon, silica, silica-alumina, alumina, zirconia, titania, ceria, vanadia, boron nitride, heteropolyacids, hydroxyapatite, zinc oxide, chromia, zeolites, carbon nanotubes, carbon fullerenes, and any combination thereof. The hydrogenating catalyst can be employed in any of the conventional types or structures known to the art. In an embodiment, any of the catalyst shapes and/or types discussed herein with respect to the conversion catalyst may be used with the hydrogenating catalyst.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Catalyst Example 1.

15 g of synthetic hydrotalcite were mixed with 4 g of solid Ca-hydroxide and ~50 ml water to form a thick slurry. Ethanol was added until all solids were wetted by the water. The slurry was mixed very well, dried at 105° C. followed by heating to 475° C. at a heating rate of 1° C./min and held at 475° C. for 2 hours followed by cooling to room temperature. A 7 g sample from the resulting powder was mixed into a wet paste with ~15 ml aqueous solution of 0.1025 g $Pd(NO_3)_2 \cdot 6H_2O$. The paste was dried at 105° C., and the dry powder was treated with 0.5 ml 4 M NaOH, 1 ml 35 wt. % stock aqueous methanol formaldehyde solution diluted to 7 ml with DI water. A color transformation took place indicating the reduction of the Pd salt to Pd metal. The resulting powder was pressed into pellets, broken down to uniform sizes and subjected to testing for ethanol to n-butanol and higher alcohols conversion.

Figure 8:
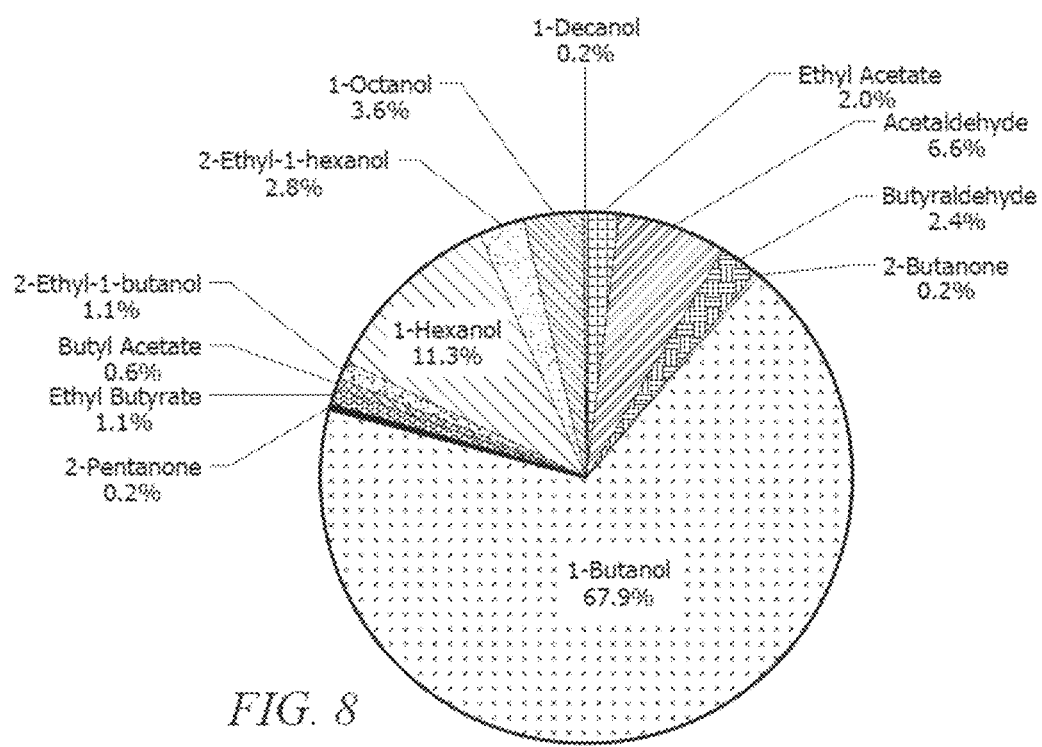
FIG. 8 illustrates a product distribution obtained by reacting ethanol over an embodiment of the catalyst.

The testing used 4.3 g of the catalyst at 260° C. and 300 psig pressure, with a flow rate of ethanol of 0.2 ml/min. The product distribution achieved is shown in FIG. 8, which illustrates an ethanol conversion of 13.9%.

Table 1 shows the ethanol conversion and selectivity to both 1-butanol and to all alcohols in the $C_4$-$C_{12}$ range at different temperatures and at testing conditions using 4.3 g of the catalyst, 300 psig pressure, and a flow rate of ethanol of 0.2 ml/min. For all examples, selectivity to 1-butanol is calculated as:

$$\text{butanol selectivity} = \frac{n_{BuOH}}{n_{0,EtOH} - n_{EtOH} - n_{ACH} - n_{BA}}$$

Where $n_{BuOH}$ is the molar flow rate of 1-butanol out of the reactor, $n_{0,EtOH}$ is the molar feed rate of ethanol into the reactor, $n_{EtOH}$ is the molar flow rate of ethanol out of the reactor, $n_{ACH}$ is the molar flow rate of acetaldehyde out of the reactor, and $n_{BA}$ is the molar flow rate of butyraldehyde out of the reactor (acetaldehyde and butyraldehyde are intermediates in the reaction chemistry from ethanol to 1-butanol). The $C_4$-$C_{12}$ alcohol selectivity is calculated as:

$$C4 - C12 \text{ alcohol selectivity} = \frac{n_{BuOH} + n_{C5-C12}}{n_{0,EtOH} - n_{EtOH} - n_{ACH} - n_{BA}}$$

Where $n_{BuOH}$, $n_{0,EtOH}$, $n_{EtOH}$, $n_{ACH}$, and $n_{BA}$ are the same as described above and $n_{C5-C12}$ is the total molar flow rate of all alcohols with 5 to 12 carbons.

TABLE 1

Conversion and selectivity for ethanol to butanol and higher alcohols over catalyst

| Temp (° C.) | Ethanol Conversion (%) | Butanol Selectivity (%) | C4-C12 alcohol selectivity (%) |
|---|---|---|---|
| 220 | 6 | 75 | 96 |
| 230 | 8 | 65 | 96 |
| 240 | 10 | 72 | 96 |
| 250 | 12 | 69 | 96 |
| 260 | 14 | 73 | 96 |
| 270 | 13 | 77 | 96 |
| 280 | 17 | 76 | 95 |

Example 2

Catalyst Example 2.

10 g of synthetic hydrotalcite were mixed with 1 g Mg-acetate tetrahydrate dissolved in ~15-20 ml water to form a slurry. Ethanol was added in small portions until all hydrotalcite particles were wetted by the aqueous phase. The slurry was mixed very well, dried at 105° C. followed by heating to 475° C. at a heating rate of 1° C./min and held at 475° C. for 2 hours followed by cooling to room temperature. A 5.5 g sample from the resulting powder was mixed into a wet paste with ~15 ml aqueous solution of 0.1004 g Pd(NO$_3$)$_2$·6H$_2$O. The paste was dried at 105° C. The dry powder was heated to 475° C. at 1° C./min. and held at 475° C. for 2 hours then cooled down.

Figure 9:
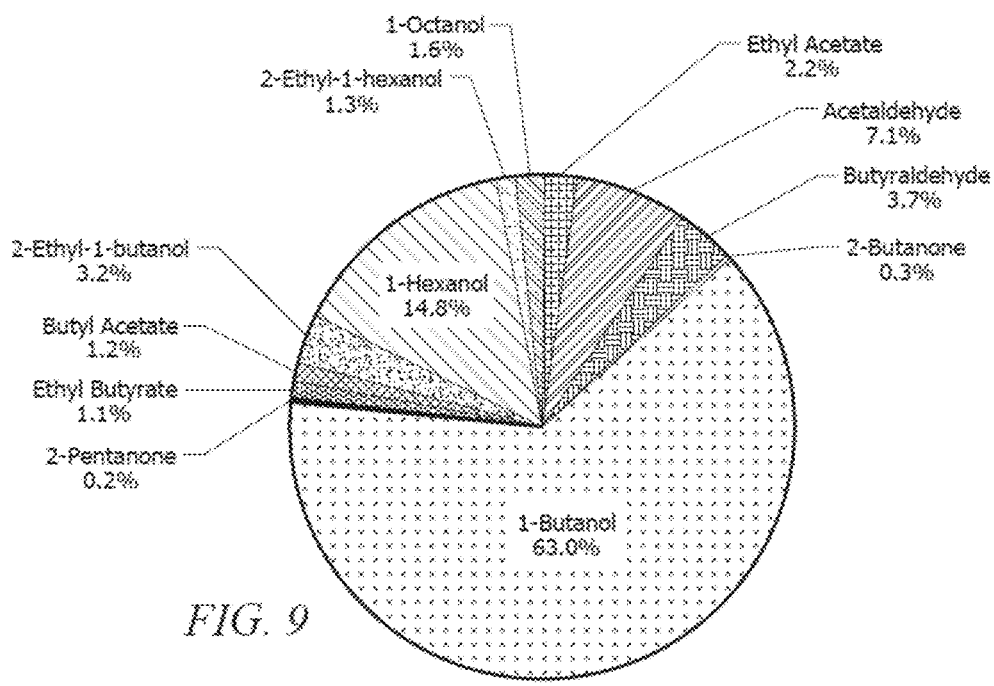
FIG. 9 illustrates another product distribution obtained by reacting ethanol over another embodiment of the catalyst.

The resulting catalyst powder was pressed in pellets, broken down to uniform sizes and subjected to testing for ethanol to n-butanol and higher alcohols conversion. The testing used 4.3 g of the catalyst at 260° C. and 300 psig pressure, with a flow rate of ethanol of 0.2 ml/min. The product distribution achieved is shown in FIG. 9 with an ethanol conversion of 20.2%. Table 2 shows the ethanol conversion and selectivity to both 1-butanol and to all alcohols in the C4-C12 range at different temperatures and at testing conditions using 4.3 g of the catalyst, 300 psig pressure, and a flow rate of ethanol of 0.2 ml/min.

TABLE 2

Conversion and selectivity for ethanol to butanol and higher alcohols over catalyst

| Temp (° C.) | Ethanol Conversion (%) | Butanol Selectivity (%) | C4-C12 alcohol selectivity (%) |
|---|---|---|---|
| 220 | 8 | 86 | 97 |
| 230 | 10 | 78 | 94 |
| 240 | 13 | 76 | 94 |
| 250 | 17 | 69 | 95 |
| 260 | 20 | 69 | 95 |

Example 3

Catalyst Example 3.

10 g of synthetic hydrotalcite were mixed with 4 g Ca-acetate hydrate dissolved in ~15-20 ml water to form a slurry. Ethanol was added in small portions until all hydrotalcite particles were wetted by the aqueous phase. The slurry was mixed very well, dried at 105° C. followed by heating to 475° C. at 1° C./min, and held at 475° C. for 2 hours followed by cooling to room temperature. A 5.5 g sample from the resulting powder was mixed into a wet paste with ~15 ml aqueous solution of 0.1210 g Pd(NO$_3$)$_2$·6H$_2$O. The paste was dried at 105° C. The dry powder was heated to 475° C. at a heating rate of 1° C./min, and held at 475° C. for 2 hours then cooled down.

Figure 10:
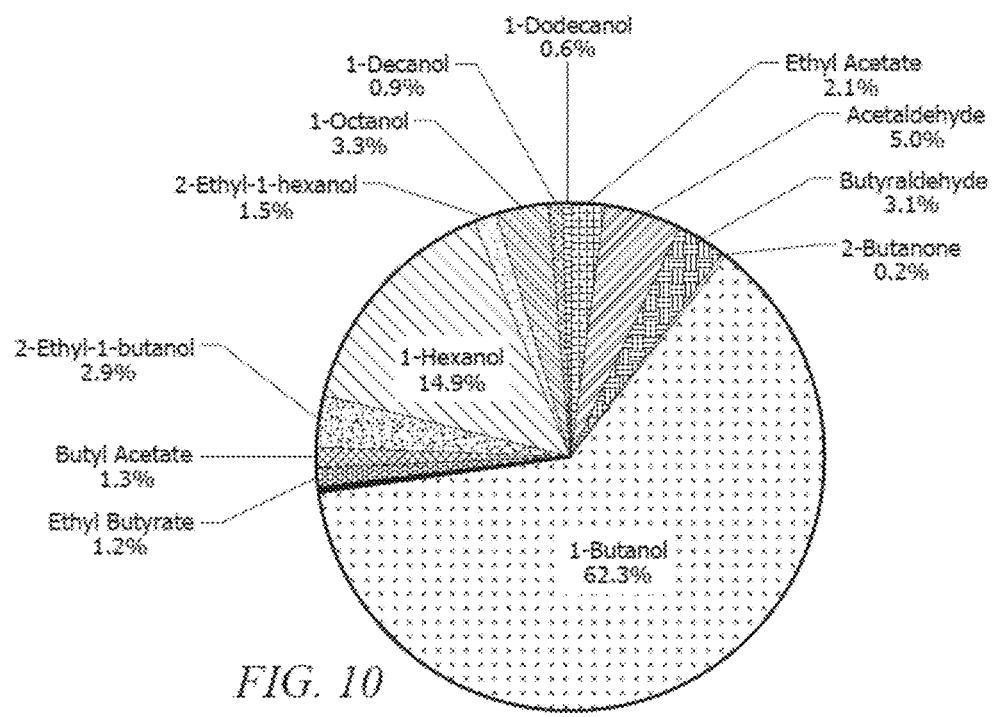
FIG. 10 illustrates another product distribution obtained by reacting ethanol over yet another embodiment of the catalyst.

The resulting catalyst powder was pressed in pellets, broken down to uniform sizes and subjected to testing for ethanol to n-butanol and higher alcohols conversion. The testing used 4.5 g of the catalyst at 260° C. and 300 psig pressure, with a flow rate of ethanol of 0.2 ml/min. The product distribution achieved is shown in FIG. 10 with an ethanol conversion of 26.2%. Table 3 shows the ethanol conversion and selectivity to both 1-butanol and to all alcohols in the C$_4$-C$_{12}$ range at different temperatures and at testing conditions using 4.5 g of the catalyst, 300 psig pressure, and a flow rate of ethanol of 0.2 ml/min.

TABLE 3

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 15 | 54 | 95 |
| 230 | 18 | 55 | 95 |
| 240 | 19 | 65 | 95 |
| 250 | 23 | 65 | 95 |
| 260 | 26 | 65 | 95 |

Example 4

Catalyst Example 4.

10 g synthetic hydrotalcite were heated to 475° C. at a heating rate of 1° C./min, and held at 475° C. for 2 hours followed by cooling to room temperature. A 5.5 g sample from the resulting powder was mixed into a wet paste with ~15 ml aqueous solution of 0.1072 g Pd(NO$_3$)$_2$·6H$_2$O. The paste was dried at 105° C. The dry powder was heated to 475° C. at a heating rate of 1° C./min, and held at 475° C. for 2 hours then cooled down.

Figure 11:
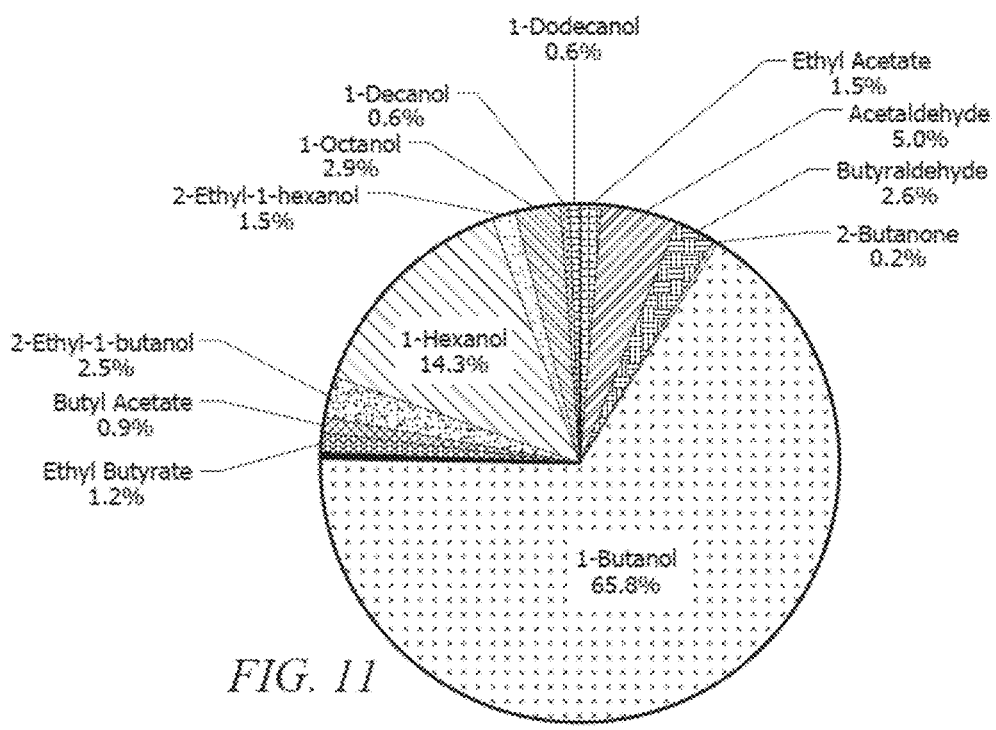
FIG. 11 illustrates another product distribution obtained by reacting ethanol over still another embodiment of the catalyst.

The resulting catalyst powder was pressed in pellets, broken down to uniform sizes and subjected to testing for ethanol to n-butanol and higher alcohols conversion. The testing used 5.0 g of the catalyst at 260° C. and 300 psig pressure, with a flow rate of ethanol of 0.2 ml/min. The product distribution achieved is shown in FIG. 11 with ethanol conversion of 25.0%. Table 4 shows the ethanol conversion and selectivity to both 1-butanol and to all alcohols in the C$_4$-C$_{12}$ range at different temperatures and at testing conditions using 5.0 g of the catalyst, 300 psig pressure, and a flow rate of ethanol of 0.2 ml/min.

TABLE 4

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 13 | 75 | 98 |
| 230 | 16 | 71 | 96 |
| 240 | 21 | 66 | 96 |
| 250 | 23 | 69 | 96 |
| 260 | 25 | 69 | 96 |

Example 5

Catalyst Example 5.

Figure 12:
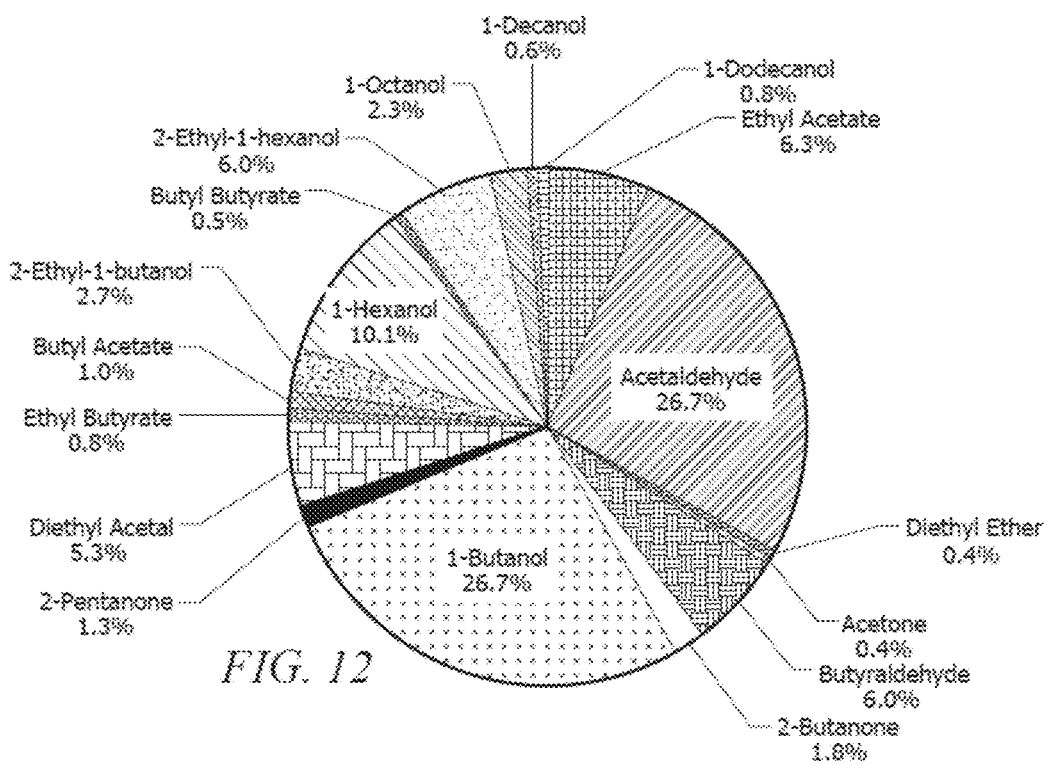
FIG. 12 illustrates another product distribution obtained by reacting ethanol over another embodiment of the catalyst.

10 g synthetic hydrotalcite were heated to 475° C. at a heating rate of 1° C./min. and held at 475° C. for 2 hours followed by cooling to room temperature. The resulting catalyst powder was pressed in pellets, broken down to uniform sizes. 0.37 g of Cu(NO$_3$)$_2$·2.5H$_2$O was dissolved in 10 ml of water and added to 10 g of silica support pellets (Saint Gobain SS61138). The silica pellets were then dried at 110° C., and then heated to 450° C. at a heating rate of 1° C./min and held at 450° C. for 2 hours before cooling to room temperature. The resulting catalyst pellets were then crushed to uniform sized (at approximately the same size as the final hydrotalcite catalyst). A physical mixture of the two catalysts was prepared by mixing 1 g of the Cu/SiO$_2$ catalyst with 5 g of hydrotalcite. This mixture was then tested in an ethanol to n-butanol (and higher alcohols) reaction at 260° C. and 300 psig pressure, with a flow rate of ethanol of 0.2 ml/min. The product distribution achieved is shown in FIG. 12 with ethanol conversion of 13.1%. Table 5 shows the ethanol conversion and selectivity to both 1-butanol and to all alcohols in the $C_4$-$C_{12}$ range at different temperatures and at testing conditions using 6.0 g of the catalyst (total), 300 psig pressure, and a flow rate of ethanol of 0.2 ml/min.

TABLE 5

Conversion and selectivity for ethanol to butanol and higher alcohols over catalyst.

| Temp (° C.) | Ethanol Conversion (%) | Butanol Selectivity (%) | C4-C12 alcohol selectivity (%) |
|---|---|---|---|
| 220 | 6 | 68 | 88 |
| 230 | 7 | 74 | 87 |
| 240 | 7 | 64 | 80 |
| 250 | 10 | 68 | 79 |
| 260 | 13 | 42 | 82 |
| 270 | 14 | 61 | 77 |
| 280 | 15 | 59 | 75 |

Example 6

Catalyst Example 6.

250 g of synthetic hydrotalcite were heated to 475° C. at a heating rate of 1° C./min and held at 475° C. for 2 hours followed by cooling to room temperature. A 200 g sample from the resulting powder was mixed into a thick paste with 200 ml of an aqueous solution of 3.64 g $Pd(NO_3)_2 \cdot 6H_2O$. The paste was extruded in a single screw extruder into ⅛ inch diameter trilobes. The resulting extrudates were dried at 105° C., and then heated to 475° C. at a heating rate of 1° C./min, held at 475° C. for 2 hours, and then cooled down.

Figure 13:
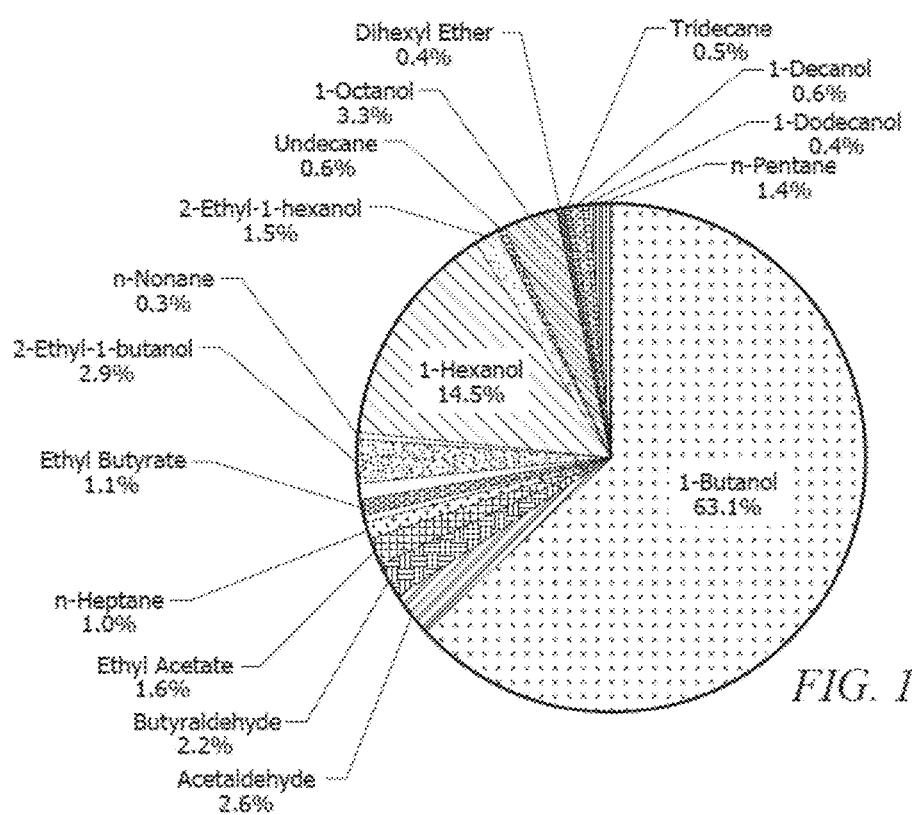
FIG. 13 illustrates another product distribution obtained by reacting ethanol over yet another embodiment of the catalyst.

The resulting catalyst pellets were broken down to uniform sizes and subjected to testing for ethanol to n-butanol and higher alcohols conversion. The testing used 5.0 g of the catalyst at 260° C. and 300 psig pressure, with a flow rate of ethanol of 0.173 ml/min. The product distribution achieved is shown in FIG. 13 with ethanol conversion of 27.6%. Table 4 shows the ethanol conversion and selectivity to both 1-butanol and to all alcohols in the $C_4$-$C_{12}$ range at different temperatures and at testing conditions using 5.0 g of the catalyst, 300 psig pressure, and a flow rate of ethanol of 0.173 ml/min.

TABLE 6

Conversion and selectivity for ethanol to butanol and higher alcohols over catalyst example 6.

| Temp (° C.) | Ethanol Conversion (%) | Butanol Selectivity (%) | C4-C12 alcohol selectivity (%) |
|---|---|---|---|
| 220 | 13 | 62 | 91 |
| 230 | 17 | 58 | 91 |
| 240 | 21 | 63 | 91 |
| 250 | 24 | 63 | 90 |
| 260 | 28 | 64 | 90 |

Example 7

Catalyst Characterizations a Brunauer-Emmett-Teller (BET) analysis was performed on the catalyst examples prepared as described above. The BET results as shown in table 7 illustrate that the thermal decomposition of the hydrotalcite starting material increases both the surface area and pore volume of the material. The higher surface area may allow for better dispersion of the Pd metal on the hydrotalcite support.

TABLE 7

BET specific surface area and pore volume results for catalyst examples 1-4 and the starting hydrotalcite.

| Sample | Surface Area ($m^2$/g) | Pore Volume ($cm^3$/g) |
|---|---|---|
| Synthetic Hydrotalcite | 8.5 | 0.0420 |
| Catalyst Example 1 | 25.2 | 0.0950 |
| Catalyst Example 2 | 69.6 | 0.2828 |
| Catalyst Example 3 | 50.8 | 0.1800 |
| Catalyst Example 4 | 54.2 | 0.3009 |

Figure 14:
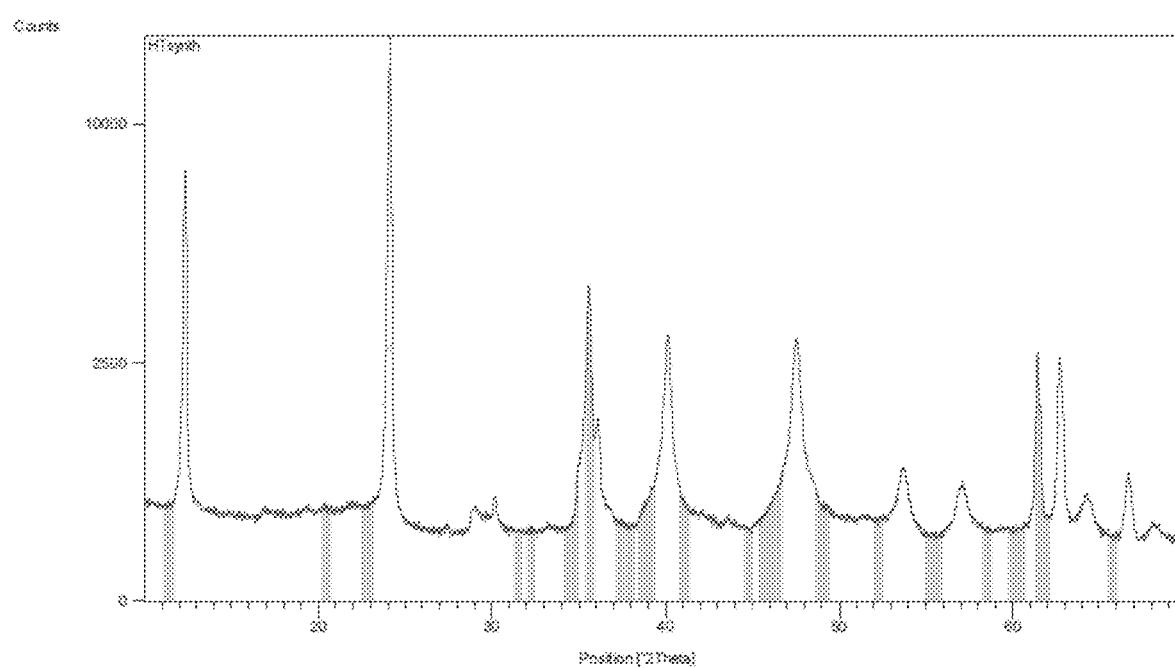
FIG. 14 illustrates an X-ray diffraction pattern of a hydrotalcite.
Figure 15:
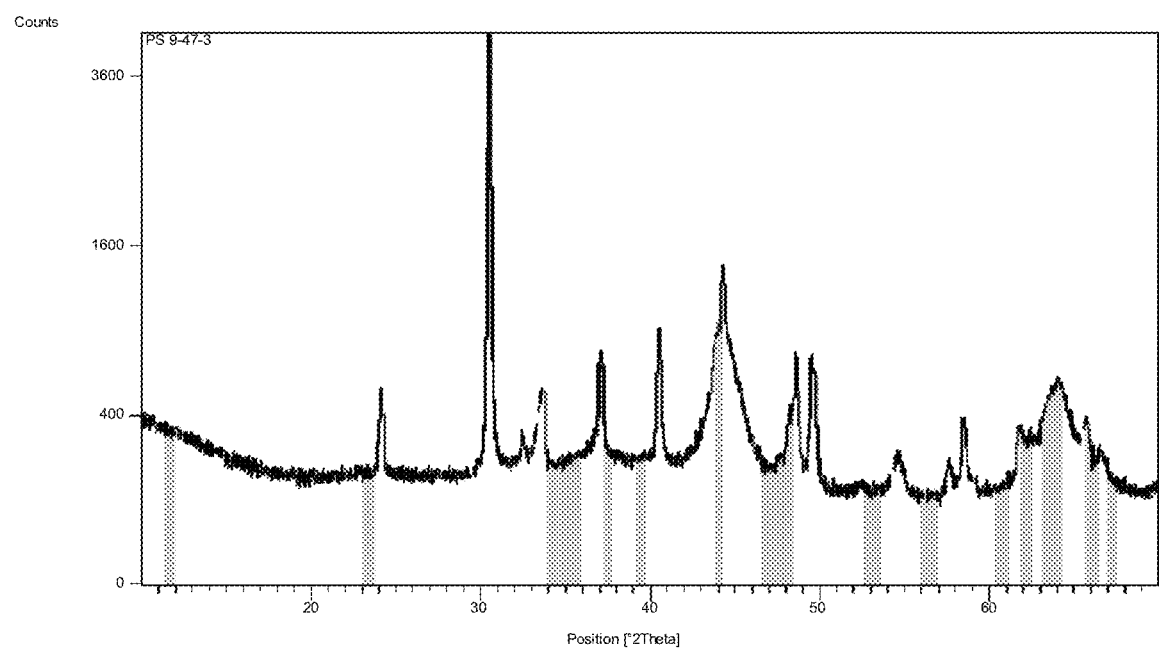
FIG. 15 illustrates an X-ray diffraction pattern of a sample of an embodiment of the catalyst.

The X-Ray Diffraction (XRD) pattern of the starting hydrotalcite material is shown in FIG. 14, and the XRD pattern of the final catalyst (Pd on decomposed hydrotalcite) is shown in FIG. 15 (illustrating the XRD pattern for the catalyst in example 3). The peaks in FIG. 15 correspond to the structure of meixnerite, which is a compound with the general structure of $Mg_6Al_2(OH)_{18} \cdot 4H_2O$. The XRD patterns for all of the catalyst examples are expected to be similar from the one presented in FIG. 15.

The XRD pattern of the synthetic hydrotalcite shows all of the typical reflections normally seen in hydrotalcite. The XRD pattern of the prepared catalyst in FIG. 15 shows that the double layered hydroxide structure of the hydrotalcite does not remain after the thermal treatment and Pd impregnation. The thermal decomposition and crystal structure changes of hydrotalcite are well documented. Upon heating hydrotalcite decomposes gradually through amorphous mixture of aluminum and magnesium oxides which at higher temperature become meixnerite ($Mg_6Al_2(OH)_{18} \cdot 4H_2O$). This is the reason for the change in the powder XRD pattern as well as the increase in the specific surface area (SSA) and pore volume as observed by BET method of nitrogen adsorption.

Example 8

Normal Impregnation of Pellets.

In this preparation of a first sample, 100 g of synthetic hydrotalcite was heated to 475° C. at 1° C./min and held at 475° C. for 2 hours followed by cooling to room temperature. The resulting powder was made into a thick dough-like consistency by adding deionized water. That was then extruded in a single screw extruder into ⅛ inch trilobes. The extrudates were dried at 105° C. and then calcined again by heating to 475° C. at 1° C./min. and holding at 475° C. for 2 hours followed by cooling to room temperature. 55 g from the resulting extrudates were mixed with ~150 ml aqueous solution of 1.072 g $Pd(NO_3)_2 \cdot 6H_2O$. The pellets were then dried at 105° C. followed by a final calcination at 475° C., heating at 1° C./min and holding at 475° C. for 2 hours before cooling to ambient temperature.

Normal Impregnation of Powder.

In this preparation of a second sample, 100 g of synthetic hydrotalcite was heated to 475° C. at 1° C./min. and held at 475° C. for 2 hours followed by cooling to room temperature. 55 g from the resulting powder were mixed into a wet paste with ~150 ml aqueous solution of 1.072 g Pd $(NO_3)_2 \cdot 6H_2O$. The paste was dried at 105° C. and then calcined at 475° C., heating at 1° C./min and holding at 475° C. for 2 hours before cooling to ambient temperature.

EDTA Impregnation of Powder.

In this preparation of a third sample, 100 g synthetic hydrotalcite was heated to 600° C. at 1° C./min. and held at 600° C. for 3 h. 3 g ethylendiamine tetraacetic acid were dissolved in 10 ml DI water by dropwise addition of 25 wt % $NH_4OH$ and stirring until the pH reached or exceeded 7. Alternatively, a pre-calculated amount equivalent to double the EDTA molar amount may be added. Separately, 2.5 g Pd-nitrate hydrate (Pd content ~39 wt %) were dissolved in 20 ml DI water. The EDTA solution and the Pd-nitrate solution were gradually mixed and stirred until a clear solution formed. To speed up the complex formation, the mixed solution was heated to approximately 45° C. The resulting solution was slowly added with intensive stirring to the heated hydrotalcite powder until all powder was uniformly coated with the light red solution to a damp solid consistency (incipient wetting process). The damp solid was dried at 90° C. for 3 h until dry followed by heating to 475° C. at 1° C./min., and held at 475° C. for 2 h and then cooled to ambient temperature.

The three catalyst samples described in this example were tested for Pd dispersion by hydrogen chemisorption. Table 8 shows the results of those tests. The very low dispersion from the first sample is due to the agglomeration of Pd on the surface of the catalyst pellet. The Pd forms a shell on the outside of the pellet with no Pd deposited on the interior portion of the pellet. The relatively high Pd concentration on the shell of the pellet leads to larger Pd particles. This agglomeration can be mitigated by performing the Pd deposition on the hydrotalcite powder (the second sample), however, the hydrolysis of the Pd on the basic surface is still limiting the Pd dispersion. The third sample shows that the use of a complexing agent such as EDTA in the Pd deposition further improves the metal dispersion.

TABLE 8

Pd dispersion (%) for examples 1-3 described above.
The dispersion % describes the percentage of
surface Pd atoms relative to all Pd atoms.

| Sample | Pd Dispersion (%) |
| --- | --- |
| Example 1 | 41.8 |
| Example 2 | 69.1 |
| Example 3 | 94.0 |

Example 9

Investigation of Calcination Temperature.

Figure 16:
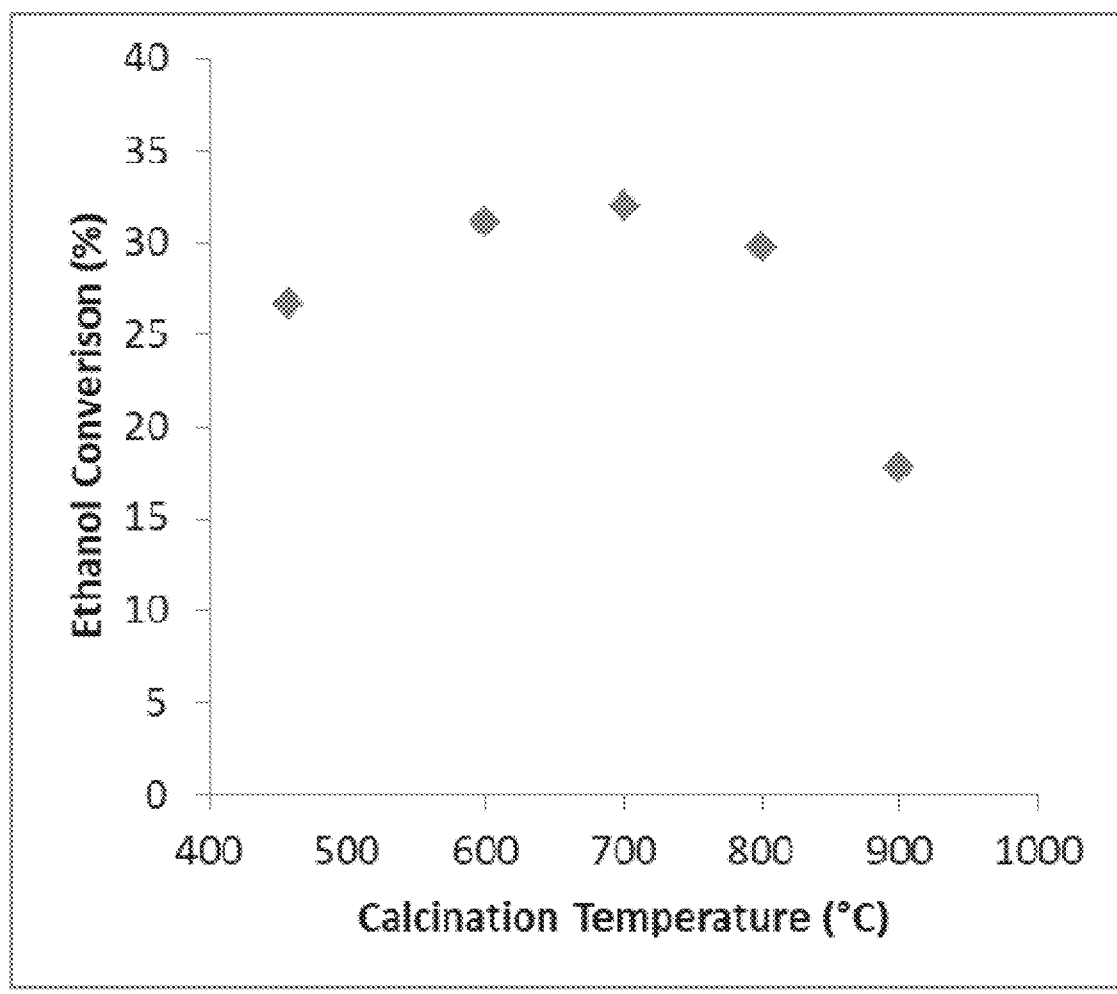
FIG. 16 illustrates a chart showing the conversion of ethanol over Pd/hydrotalcite catalysts calcined at different temperatures in a fixed bed reactor.

In this example, 100 g of synthetic hydrotalcite were heated to 475° C. at 1° C./min and held at 475° C. for 2 hours followed by cooling to room temperature. 55 g from the resulting powder were mixed into a wet paste with ~150 ml aqueous solution of 1.072 g $Pd(NO_3)_2 \cdot 6H_2O$. The paste was dried at 105° C. The dry powder was separated into several different samples and each was heated to a different final temperature at 1° C./min and held at the final temperature for 2 hours before cooling to ambient temperature. The resulting catalyst powders were pressed into pellets, broken down to uniform particle size, and then reduced in flowing hydrogen at 220° C. for 2 hours. The samples were then subjected to testing for ethanol to n-butanol and higher alcohols conversion. Samples having been calcined at different temperatures were tested under identical conditions in a fixed bed reactor. FIG. 16 shows the conversion of ethanol over Pd/hydrotalcite catalysts calcined at different temperatures in a fixed bed reactor with reactor conditions of 300 psig, 260° C., 1.9 $hr^{-1}$ WHSV ethanol feed. Ethanol conversion steadily rises as the calcination temperature increases until a temperature of 700° C., after which the conversion quickly drops as the calcination temperature rises further.

Example 10

Ester Inhibition.

A sample of Pd/hydrotalcite was prepared according to the method described in Example 9 with a second calcination temperature of 600° C. The resulting catalyst powder was pressed into pellets, broken down to uniform sizes, and then reduced in flowing hydrogen at 220° C. for 2 hours.

The performance of the resulting catalyst was evaluated in a fixed bed reactor using a pure ethanol feed to establish a baseline ethanol conversion before switching the feed to a mixture of ethanol and ethyl acetate to monitor performance with an ester impurity in the reactor feed. After establishing the effect of the ester impurity, the feed to the reactor was switched back to pure ethanol in order to evaluate any permanent change in the catalyst performance due to the impurity.

Table 9 shows the conversion of ethanol in the reactor using a pure ethanol feed and ethanol with several different concentrations of ethyl acetate. Even at ester concentrations below 1 wt % in the ethanol feed, the ester causes a significant drop in conversion.

TABLE 9

Conversion of ethanol to n-butanol and higher alcohols
in a fixed bed reactor using feeds of pure ethanol
and ethanol with an ethyl acetate impurity. Reactor conditions:
300 psig, 260° C., 1.25 $hr^{-1}$ LHSV

| Ethyl acetate content in ethanol feed (wt %) | Conversion with pure ethanol (%) | Conversion with ester impurity (%) | % loss in Conversion |
| --- | --- | --- | --- |
| 0.68 | 26.6 | 24.1 | 19.6 |
| 0.26 | 27.2 | 24.9 | 8.5 |
| 0.16 | 25.3 | 23.7 | 6.3 |
| 0.08 | 25.9 | 24.3 | 6.2 |
| 0.04 | 25.6 | 24.7 | 3.5 |
| 0.02 | 25.4 | 25.1 | 1.2 |

The drop in performance due to the ester impurity is recovered upon switching the feed to the reactor back to pure ethanol. This indicates that the ester is acting as an inhibitor to the reaction and not as a catalyst poison.

Example 11

Ester Inhibition.

In order to verify that all esters will behave as reaction inhibitors, the test from Example 10 was repeated using ethyl butyrate in place of ethyl acetate. Table 10 shows that the catalyst performance is similarly reduced when ethyl butyrate is the impurity added to the ethanol feed.

TABLE 10

Conversion of ethanol to n-butanol and higher alcohols in a fixed bed reactor using feeds of pure ethanol and ethanol with an ethyl butyrate impurity. Reactor conditions: 300 psig, 260° C., 1.25 hr$^{-1}$ LHSV

| Ethyl butyrate content in ethanol feed (wt %) | Conversion with pure ethanol (%) | Conversion with ester impurity (%) | % loss in Conversion |
|---|---|---|---|
| 0.43 | 26.7 | 22.8 | 14.6 |
| 0.18 | 25.2 | 23.9 | 6.3 |

As in the case with ethyl acetate as the impurity, the catalyst recovers its initial activity when the reactor feed is switched from the mixture of ethanol and ethyl butyrate back to pure ethanol.

Having described the various methods, systems, and formulations herein, some embodiments can include, but are not limited to:

In a first embodiment, a method of producing a catalyst comprises: forming a decomposed material comprising a decomposed hydrotalcite, a decomposed hydrocalumite, or a combination of both; combining the decomposed material with a mixture to form a catalyst mixture, wherein the mixture comprises a metal salt and a chelating agent; and heating the catalyst mixture to convert the metal salt to a metal oxide, wherein the resulting metal oxide combined with the decomposed material forms the catalyst.

A second embodiment can include the method of the first embodiment, wherein forming the decomposed material comprises heating a material comprising hydrotalcite, hydrocalumite, or both, above a decomposition temperature.

A third embodiment can include the method of the second embodiment, wherein heating the material comprises heating the material to a temperature between about 600° C. and about 750° C. for a time sufficient to decompose the material.

A fourth embodiment can include the method of any one of the first to third embodiments, wherein the metal salt comprises at least one metal ion, and wherein the mixture comprises a molar ratio of the chelating agent to the at least one metal ion between about 0.5:1 to about 3:1.

A fifth embodiment can include the method of any one of the first to fourth embodiments, wherein the process further comprises: mixing a second metal salt with the material prior to heating the material.

A sixth embodiment can include the method of the fifth embodiment, wherein mixing the second metal salt with the material comprises mixing the second metal salt as a second mixture, wherein the second mixture comprises at least one chelating agent.

A seventh embodiment can include the method of the sixth embodiment, wherein the second metal salt comprises an alkaline salt, an alkaline earth salt, or any combination thereof.

An eighth embodiment can include the method of any one of the first to seventh embodiments, wherein the metal salt comprises one or more metals selected from the group consisting of: Pd, Cu, Pt, Cr, Ni, Fe, Ru, Rh, and Co.

A ninth embodiment can include the method of any one of the first to eighth embodiments, wherein the catalyst has a surface area of between about 20 m$^2$/g to about 100 m$^2$/g.

A tenth embodiment can include the method of any one of the first to ninth embodiments, wherein the catalyst has a pore volume of between about 0.05 cm$^3$/g and about 0.4 cm$^3$/g.

An eleventh embodiment can include the method of any one of the first to tenth embodiments, wherein the process further comprises combining the catalyst with a support material.

A twelfth embodiment can include the method of any one of the first to eleventh embodiments, further comprising: extruding the decomposed material into a granule prior to combining the decomposed material with the metal salt to form the catalyst mixture.

A thirteenth embodiment can include the method of any one of the first to twelfth embodiments, further comprising: extruding the catalyst mixture into a granule.

In a fourteenth embodiment, a method of producing a catalyst comprises: combining a material with a mixture to form a catalyst mixture, wherein the material comprises hydrotalcite, hydrocalumite, or both, and wherein the mixture comprises a metal salt and a chelating agent; and decomposing the catalyst mixture above a decomposition temperature of the material to form a decomposed material; and heating the catalyst mixture to convert the metal salt to a metal oxide, wherein the resulting metal oxide combined with the decomposed material forms the catalyst.

A fifteenth embodiment can include the method of the fourteenth embodiment, wherein at least one of decomposing the catalyst mixture or heating the catalyst mixture comprises heating the catalyst mixture to a temperature between about 600° C. and about 750° C. for a time sufficient to decompose the material.

A sixteenth embodiment can include the method of the fourteenth or fifteenth embodiment, wherein the metal salt comprises at least one metal ion, and wherein the mixture comprises a molar ratio of the chelating agent to the at least one metal ion between about 0.5:1 to about 3:1.

A seventeenth embodiment can include the method of any one of the fourteenth to sixteenth embodiments, wherein the metal salt comprises one or more metals selected from the group consisting of: Pd, Cu, Pt, Cr, Ni, Fe, Ru, Rh, and Co.

An eighteenth embodiment can include the method of any one of the fourteenth to seventeenth embodiments, wherein the catalyst has a surface area of between about 20 m$^2$/g to about 100 m$^2$/g.

A nineteenth embodiment can include the method of any one of the fourteenth to eighteenth embodiments, wherein the catalyst has a pore volume of between about 0.05 cm$^3$/g and about 0.4 cm$^3$/g.

A twentieth embodiment can include the method of any one of the fourteenth to nineteenth embodiments, wherein the process further comprises combining the catalyst with a support material.

A twenty first embodiment can include the method of any one of the fourteenth to twentieth embodiments, further comprising: extruding the decomposed material into a granule prior to combining the decomposed material with the metal salt to form the catalyst mixture.

A twenty second embodiment can include the method of any one of the fourteenth to twenty first embodiments, further comprising: extruding the catalyst mixture into a granule.

In a twenty third embodiment, a method of producing a catalyst comprises: decomposing material to form a decomposed hydrotalcite, a decomposed hydrocalumite, or a combination of both; combining the decomposed material with a mixture to form a catalyst mixture, wherein the mixture comprises a metal salt; and heating the catalyst mixture to convert the metal salt to a metal oxide, wherein the resulting metal oxide combined with the decomposed material forms the catalyst, and wherein at least one of the decomposing or the heating comprises applying heat at a temperature between 600° C. and 750° C.

A twenty fourth embodiment can include the method of the twenty third embodiment, wherein forming the decomposed material comprises heating a material comprising hydrotalcite, hydrocalumite, or both, to a temperature in a range of 350° C. to 800° C.

A twenty fifth embodiment can include the method of the twenty fourth embodiment, wherein heating the catalyst mixture comprises heating the material to a temperature between about 300° C. and about 800° C.

A twenty sixth embodiment can include the method of any one of the twenty third to twenty fifth embodiments, wherein the process further comprises: mixing a second metal salt with the material prior to heating the material.

A twenty seventh embodiment can include the method of the twenty sixth embodiment, wherein the second metal salt comprises an alkaline salt, an alkaline earth salt, or any combination thereof.

A twenty eighth embodiment can include the method of any one of the twenty third to twenty seventh embodiments, wherein the metal salt comprises one or more metals selected from the group consisting of: Pd, Cu, Pt, Cr, Ni, Fe, Ru, Rh, and Co.

In a twenty ninth embodiment, a method for producing a higher alcohol comprises: contacting a reactant comprising ethanol with a catalyst at a reaction temperature and pressure sufficient to produce a reaction product, wherein the catalyst comprises a decomposed hydrotalcite, a decomposed hydrocalumite, or a combination of both mixed with one or more metal oxides, wherein the reaction product comprises a higher alcohol, unreacted ethanol, and an ester; separating the unreacted ethanol from the reaction product; separating substantially all of the ester from the unreacted ethanol to form an ethanol recycle stream; and recycling the ethanol recycle stream to contact the catalyst.

A thirtieth embodiment can include the method of the twenty ninth embodiment, wherein the higher alcohol is butanol.

A thirty first embodiment can include the method of the twenty ninth embodiment, wherein the higher alcohol comprises a $C_4$-$C_{13}$ alcohol.

A thirty second embodiment can include the method of the twenty ninth embodiment, wherein a conversion of ethanol to the higher alcohol is at least about 10%.

A thirty third embodiment can include the method of the twenty ninth embodiment, wherein a selectivity of the conversion of ethanol to the higher alcohol is at least about 90%.

A thirty fourth embodiment can include the method of the twenty ninth embodiment, wherein the one or more metal oxides comprise one or more metals selected from the group consisting of: Pd, Cu, Pt, Cr, Ni, Fe, Ru, Rh, and Co.

A thirty fifth embodiment can include the method of the twenty ninth embodiment, wherein the one or more metal oxides comprises an alkaline salt, an alkaline earth salt, or any combination thereof.

A thirty sixth embodiment can include the method of the twenty ninth embodiment, wherein the catalyst further comprises a support material.

A thirty seventh embodiment can include the method of any one of the twenty ninth to thirty sixth embodiments, wherein the reactant and the ethanol recycle stream are substantially free of esters.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method of producing a catalyst comprising:
   forming a decomposed material comprising a decomposed hydrotalcite, a decomposed hydrocalumite, or a combination of both;
   combining the decomposed material with a mixture to form a catalyst mixture, wherein the mixture comprises a metal salt and a chelating agent; and
   heating the catalyst mixture to convert the metal salt to a metal oxide, wherein the resulting metal oxide combined with the decomposed material forms the catalyst.

2. The method of claim 1, wherein forming the decomposed material comprises heating a material comprising hydrotalcite, hydrocalumite, or both, above a decomposition temperature.

3. The method of claim 2, wherein heating the material comprises heating the material to a temperature between about 600° C. and about 750° C. for a time sufficient to decompose the material.

4. The method of claim 1, wherein the metal salt comprises at least one metal ion, and wherein the mixture comprises a molar ratio of the chelating agent to the at least one metal ion between about 0.5:1 to about 3:1.

5. The method of claim 1, wherein the process further comprises: mixing a second metal salt with the decomposed material prior to heating the decomposed material.

6. The method of claim 5, wherein mixing the second metal salt with the decomposed material comprises mixing the second metal salt as a second mixture, wherein the second mixture comprises at least one chelating agent.

7. The method of claim 6, wherein the second metal salt comprises an alkaline salt, an alkaline earth salt, or any combination thereof.

8. The method of claim 1, wherein the metal salt comprises one or more metals selected from the group consisting of: Pd, Cu, Pt, Cr, Ni, Fe, Ru, Rh, and Co.

9. The method of claim 1, wherein the catalyst has a surface area of between about 20 $m^2/g$ to about 100 $m^2/g$.

10. The method of claim 1, wherein the catalyst has a pore volume of between about 0.05 $cm^3/g$ and about 0.4 $cm^3/g$.

11. The method of claim 1, wherein the process further comprises combining the catalyst with a support material.

12. The method of claim 1, further comprising:
extruding the decomposed material into a granule prior to combining the decomposed material with the metal salt to form the catalyst mixture.

13. The method of claim 1, further comprising: extruding the catalyst mixture into a granule.

14. A method of producing a catalyst comprising:
combining a material with a mixture to form a catalyst mixture, wherein the material comprises hydrotalcite, hydrocalumite, or both, and wherein the mixture comprises a metal salt and a chelating agent; and
decomposing the catalyst mixture above a decomposition temperature of the material to form a decomposed material; and
heating the catalyst mixture to convert the metal salt to a metal oxide, wherein the resulting metal oxide combined with the decomposed material forms the catalyst.

15. The method of claim 14, wherein at least one of decomposing the catalyst mixture or heating the catalyst mixture comprises heating the catalyst mixture to a temperature between about 600° C. and about 750° C. for a time sufficient to decompose the material.

16. The method of claim 14, wherein the metal salt comprises at least one metal ion, and wherein the mixture comprises a molar ratio of the chelating agent to the at least one metal ion between about 0.5:1 to about 3:1.

17. The method of claim 14, wherein the metal salt comprises one or more metals selected from the group consisting of: Pd, Cu, Pt, Cr, Ni, Fe, Ru, Rh, and Co.

18. The method of claim 14, wherein the catalyst has a surface area of between about 20 $m^2/g$ to about 100 $m^2/g$.

19. The method of claim 14, wherein the catalyst has a pore volume of between about 0.05 $cm^3/g$ and about 0.4 $cm^3/g$.

20. The method of claim 14, wherein the process further comprises combining the catalyst with a support material.

21. The method of claim 14, further comprising:
extruding the material into a granule prior to combining the material with the metal salt to form the catalyst mixture.

22. The method of claim 14, further comprising: extruding the catalyst mixture into a granule.

* * * * *